(12) United States Patent
McKinney et al.

(10) Patent No.: US 10,813,589 B2
(45) Date of Patent: **\*Oct. 27, 2020**

(54) CATHETER FOR MONITORING UTERINE CONTRACTION PRESSURE

(71) Applicant: Sentinel Medical Technologies, LLC, Boca Raton, FL (US)

(72) Inventors: Timothy McKinney, Boca Raton, FL (US); Marc-Alan Levine, Pottstown, PA (US)

(73) Assignee: Sentinel Medical Technologies, LLC, Boca Raton, FL (US)

( * ) Notice: Subject to any disclaimer, the term of this patent is extended or adjusted under 35 U.S.C. 154(b) by 291 days.

This patent is subject to a terminal disclaimer.

(21) Appl. No.: 15/949,022

(22) Filed: Apr. 9, 2018

(65) Prior Publication Data

US 2018/0344250 A1 Dec. 6, 2018

Related U.S. Application Data

(60) Provisional application No. 62/544,690, filed on Aug. 11, 2017, provisional application No. 62/514,793, (Continued)

(51) Int. Cl.
*A61B 5/00* (2006.01)
*A61M 25/10* (2013.01)
(Continued)

(52) U.S. Cl.
CPC ........ *A61B 5/6853* (2013.01); *A61B 5/02055* (2013.01); *A61B 5/033* (2013.01);
(Continued)

(58) Field of Classification Search
CPC ... A61B 5/6853; A61B 5/02055; A61B 5/033; A61B 5/035; A61B 5/4352;
(Continued)

(56) References Cited

U.S. PATENT DOCUMENTS 3,721,229 A 3/1973 Panzer
4,192,319 A 3/1980 Hargens et al.
(Continued)

FOREIGN PATENT DOCUMENTS

CA 2961757 3/2016
CN 205649494 10/2016
(Continued)

OTHER PUBLICATIONS

Devoe, LD, et al. "Monitoring intrauterine pressure during active labor. A prospective comparison of two methods", J Reprod Med. Oct. 1989; 34(10): 811-814.
(Continued)

*Primary Examiner* — Lindsey G Wehrheim
(74) *Attorney, Agent, or Firm* — Neil D. Gershon

(57) ABSTRACT

A multi-lumen catheter for monitoring uterine contraction pressure having an elongated body configured and dimensioned for insertion into a bladder of a patient, the catheter having a first lumen, a second lumen, and a first balloon at a distal portion, the first lumen communicating with the first balloon. The second lumen communicates with the bladder to remove fluid from the bladder. The first balloon is filled with a gas to form along with the first lumen a gas filled chamber to monitor pressure within the bladder to thereby monitor uterine contraction pressure of the patient.

20 Claims, 31 Drawing Sheets

Related U.S. Application Data filed on Jun. 3, 2017, provisional application No. 62/590,513, filed on Nov. 24, 2017, provisional application No. 62/622,871, filed on Jan. 27, 2018.

(51) Int. Cl.

| | | |
|---|---|---|
| *A61M 31/00* | (2006.01) | |
| *A61B 5/03* | (2006.01) | |
| *A61M 39/10* | (2006.01) | |
| *A61B 5/0205* | (2006.01) | |
| *A61M 39/08* | (2006.01) | |
| *A61M 25/00* | (2006.01) | |
| *A61M 25/04* | (2006.01) | |
| *A61B 5/01* | (2006.01) | |
| *A61B 5/024* | (2006.01) | |
| *A61B 5/145* | (2006.01) | |

(52) U.S. Cl.
CPC .......... *A61B 5/035* (2013.01); *A61B 5/4362* (2013.01); *A61M 25/1011* (2013.01); *A61M 31/005* (2013.01); *A61M 39/10* (2013.01); *A61M 39/105* (2013.01); *A61B 5/01* (2013.01); *A61B 5/02411* (2013.01); *A61B 5/14503* (2013.01); *A61B 5/14542* (2013.01); *A61M 25/0097* (2013.01); *A61M 25/04* (2013.01); *A61M 2025/0002* (2013.01); *A61M 2025/0003* (2013.01); *A61M 2025/1013* (2013.01); *A61M 2025/1061* (2013.01); *A61M 2039/082* (2013.01)

(58) Field of Classification Search
CPC .......... A61M 25/1011; A61M 31/005; A61M 39/10; A61M 39/105; A61M 25/0097; A61M 25/04; A61M 2025/0002; A61M 2025/0003; A61M 2025/1013; A61M 2025/1061; A61M 2039/082
See application file for complete search history.

(56) References Cited

U.S. PATENT DOCUMENTS

| | | | |
|---|---|---|---|
| 4,739,769 A | 4/1988 | Mathews et al. | |
| 4,873,986 A | 10/1989 | Wallace | |
| 4,901,731 A | 2/1990 | Millar | |
| 5,167,237 A | 12/1992 | Rabin | |
| 5,447,497 A | 5/1995 | Sogard et al. | |
| 5,433,216 A | 7/1995 | Sugrue | |
| 5,551,439 A | 9/1996 | Hickey | |
| 5,570,671 A | 11/1996 | Hickey | |
| 5,573,007 A | 11/1996 | Bobo, Sr. | |
| 5,697,375 A | 12/1997 | Hickey | |
| 5,707,358 A | 1/1998 | Wright | |
| 5,951,497 A | 9/1999 | Wallace et al. | |
| 5,980,485 A | 11/1999 | Grantz et al. | |
| 5,984,879 A | 11/1999 | Wallace et al. | |
| 6,021,781 A | 2/2000 | Thompson et al. | |
| 6,183,421 B1 | 2/2001 | Bobo | |
| 6,231,524 B1 | 5/2001 | Wallace et al. | |
| 6,434,418 B1 | 8/2002 | Neal et al. | |
| 6,447,462 B1 | 8/2002 | Wallace et al. | |
| 6,461,332 B1 | 10/2002 | Mosel et al. | |
| 6,648,879 B2 | 11/2003 | Joye et al. | |
| 6,673,022 B1 | 1/2004 | Bobo et al. | |
| 6,723,053 B2 | 4/2004 | Ackerman et al. | |
| 6,827,710 B1 | 12/2004 | Mooney et al. | |
| 7,347,822 B2 | 3/2008 | Brockway et al. | |
| 7,381,190 B2 | 6/2008 | Sugrue et al. | |
| 7,654,967 B2 | 2/2010 | Bobo, Sr. | |
| 7,722,544 B2 | 5/2010 | Williams et al. | |
| 8,192,368 B2 | 6/2012 | Woodruff et al. | |
| 8,235,426 B2 | 8/2012 | Pisula, Jr. et al. | |
| 8,337,411 B2 | 12/2012 | Nishtala et al. | |
| 8,360,988 B2 | 1/2013 | Bobo, Sr. et al. | |
| 8,403,884 B2 | 3/2013 | Nishtala | |
| 8,535,237 B2 | 9/2013 | Nishtala | |
| 8,596,688 B2 | 12/2013 | Pisula, Jr. et al. | |
| 8,636,724 B2 | 1/2014 | Wiita et al. | |
| 8,646,325 B2 | 2/2014 | Hoem et al. | |
| 8,708,927 B2 | 4/2014 | Dijkman | |
| 8,876,729 B2 | 11/2014 | Bobo, Sr. et al. | |
| 9,046,205 B2 | 6/2015 | Whitaker et al. | |
| 9,101,314 B2 | 8/2015 | Shi | |
| 9,126,008 B2 | 9/2015 | Kim | |
| 9,393,353 B2 | 7/2016 | Alam et al. | |
| 9,439,600 B2 | 9/2016 | Mohl | |
| 9,440,043 B2 | 9/2016 | Arora et al. | |
| 9,510,766 B2 | 12/2016 | Weed et al. | |
| 9,511,209 B2 | 12/2016 | Drasler et al. | |
| 9,534,721 B2 | 1/2017 | Lombardi, III | |
| 9,622,670 B2 | 4/2017 | Burnett et al. | |
| 9,623,201 B2 | 4/2017 | Gregory et al. | |
| 9,655,555 B2 | 5/2017 | Burnett et al. | |
| 9,662,058 B2 | 5/2017 | Burnett et al. | |
| 9,662,670 B2 | 5/2017 | Veis et al. | |
| 9,695,966 B2 | 7/2017 | Lombardi, III et al. | |
| 9,734,706 B2 | 8/2017 | Moon et al. | |
| 9,931,044 B2 | 4/2018 | Burnett et al. | |
| 9,931,122 B2 | 4/2018 | Burnett et al. | |
| 10,004,551 B2 | 6/2018 | Burnett | |
| 10,238,307 B2 | 3/2019 | Schlumpf et al. | |
| 10,433,741 B2 | 10/2019 | Stimpson | |
| 2002/0183628 A1 | 12/2002 | Reich et al. | |
| 2003/0060800 A1 | 3/2003 | Ryan | |
| 2003/0114835 A1 | 6/2003 | Noda | |
| 2004/0127813 A1 | 7/2004 | Schwamm | |
| 2004/0171942 A1 | 9/2004 | Ackerman et al. | |
| 2005/0055043 A1 | 3/2005 | Foltz | |
| 2005/0065408 A1 | 3/2005 | Benderev | |
| 2005/0187430 A1 | 8/2005 | Aundal et al. | |
| 2005/0240211 A1 | 10/2005 | Sporri | |
| 2005/0283092 A1 | 12/2005 | Gedebov | |
| 2007/0083126 A1 | 4/2007 | Marko et al. | |
| 2007/0282219 A1 | 12/2007 | Holte | |
| 2008/0027358 A1 | 1/2008 | Gregersen et al. | |
| 2008/0077043 A1 | 3/2008 | Malbrain et al. | |
| 2008/0103408 A1 | 5/2008 | Denton et al. | |
| 2008/0146990 A1 | 6/2008 | Jenson et al. | |
| 2009/0221993 A1 | 9/2009 | Sohi et al. | |
| 2010/0056952 A1 | 3/2010 | Liu | |
| 2010/0094204 A1 | 4/2010 | Nishtala | |
| 2010/0094328 A1 | 4/2010 | O'dea et al. | |
| 2010/0113939 A1 | 5/2010 | Mashimo et al. | |
| 2010/0249663 A1 | 9/2010 | Nishtala | |
| 2012/0041334 A1 | 2/2012 | Goedje et al. | |
| 2012/0179063 A1 | 7/2012 | Bharucha et al. | |
| 2012/0316460 A1 | 12/2012 | Stout | |
| 2012/0316461 A1 | 12/2012 | Liu | |
| 2013/0030262 A1 | 1/2013 | Burnett et al. | |
| 2013/0066166 A1 | 3/2013 | Burnett et al. | |
| 2013/0079662 A1 | 3/2013 | Damaser et al. | |
| 2014/0155745 A1 | 6/2014 | Duncan | |
| 2014/0200482 A1 | 7/2014 | Shi | |
| 2015/0042406 A1 | 2/2015 | Kovac et al. | |
| 2015/0133799 A1 | 5/2015 | O'Connell et al. | |
| 2015/0327836 A1 | 11/2015 | Stone et al. | |
| 2015/0342512 A1 | 12/2015 | Shi | |
| 2015/0366498 A1 | 12/2015 | Choi et al. | |
| 2016/0029912 A1 | 2/2016 | Stimpson | |
| 2016/0066831 A1 | 3/2016 | Hyde et al. | |
| 2016/0074581 A1 | 3/2016 | Gerrans | |
| 2016/0106323 A1 | 4/2016 | Ou et al. | |
| 2016/0183819 A1 | 6/2016 | Burnett et al. | |
| 2016/0331294 A1 | 11/2016 | Imran et al. | |
| 2016/0331451 A1 | 11/2016 | Nabutovsky et al. | |
| 2016/0354028 A1 | 12/2016 | Damaser et al. | |
| 2016/0374576 A1 | 12/2016 | Ziaie et al. | |
| 2017/0055874 A1 | 3/2017 | Papirov et al. | |
| 2017/0071566 A1 | 3/2017 | Hart et al. | |
| 2017/0100561 A1 | 4/2017 | Burnett | |
| 2017/0128012 A1 | 5/2017 | Parks et al. | |
| 2017/0136209 A1 | 5/2017 | Burnett et al. | |

(56) References Cited

U.S. PATENT DOCUMENTS

| | | | |
|---|---|---|---|
| 2017/0156610 A1 | 6/2017 | Quackenbush et al. | |
| 2017/0156611 A1 | 6/2017 | Burnett et al. | |
| 2017/0160175 A1 | 6/2017 | Ai-Mayah | |
| 2017/0258345 A1 | 9/2017 | Smith | |
| 2017/0259035 A1 | 9/2017 | Smith et al. | |
| 2017/0332955 A1 | 11/2017 | Burnett et al. | |
| 2018/0177458 A1 | 6/2018 | Burnett et al. | |
| 2018/0184929 A1 | 7/2018 | Burnett et al. | |
| 2018/0344183 A1 | 12/2018 | McKinney et al. | |
| 2018/0344184 A1 | 12/2018 | McKinney et al. | |
| 2018/0344234 A1* | 12/2018 | McKinney | A61B 5/036 |
| 2019/0282109 A1 | 9/2019 | Schlumpf et al. | |

FOREIGN PATENT DOCUMENTS

| | | |
|---|---|---|
| EP | 0097454 A2 | 1/1984 |
| WO | WO 1995/012351 | 5/1995 |
| WO | WO 2005/013834 | 2/2005 |
| WO | WO 2006/060248 | 6/2006 |
| WO | WO 2011/053500 | 5/2011 |
| WO | WO 2012/006624 | 1/2012 |
| WO | WO 2014/160300 | 10/2014 |
| WO | WO 2014/210453 | 12/2014 |
| WO | WO 2015/191125 | 12/2015 |
| WO | WO 2016/049654 | 3/2016 |
| WO | WO 2016/204631 | 12/2016 |
| WO | WO 2017/156451 | 9/2017 |
| WO | WO 2018/136306 | 7/2018 |

OTHER PUBLICATIONS

Wilmink FA, et al., "Fetal complications after placement of an intrauterine pressure catheter: a report of two cases and review of the literature". J Matem Fetal Neonate Med 2008;21:880-883.

International search report and written opinion for international application PCT/US2018/028687 dated Sep. 28, 2018.

International search report and written opinion for international application PCT/US2018/028693 dated Sep. 28, 2018.

International search report for international application PCT/US2018/034781 dated Sep. 5, 2018.

International search report for international application PCT/US2018/032467 dated Sep. 5, 2018.

Iberti TJ, Lieber CE, Benjamin E., "Determination of Intra-abdominal Pressure Using a Transurethral Bladder Catheter: Clinical Validation of the Technique," Anesthesiology, Jan. 1989, 70(1), 47-50.

Sascha S., et al., "Pressure Measurement Techniques for Abdominal Hypertension: Conclusions from an Experimental Model", Crit Care Res Pract., May 2015: 278139.

Muller, M., et al., "A randomiied comparison of microtip and air-charged catheter for the measurement of maximum urethral closure pressure", Ginekol Pol. 2012, 83: 586-589.

"Dystocia and Augmentation of Labor", ACOG practice bulletin No. 49 Washington, DC: American College of Obstetricians and Gynecologist, Dec. 2003: 1445-1454.

Bakker, J., et al, "Outcomes after internal verses External Tocodynamometry for Monitoring Labor", The N Engl J Med, 2010, 362:306-3013.

Euliano T., et al., "Monitoring uterine activity during labor: a comparison of 3 methods", Am J Obstet Gynecol. Jan. 2013; 208:66, 1-6.

Matsuo K, Lynch MA, Kopelman JN, Atlas RO. "Anaphylactoid syndrome of pregnancy immediately after intrauterine pressure catheter placement". Am J Obstet Gynecol 2008; 198: e8-e9.

D.J. Sawchuck, B.K. Wittmann "Pre-eclampsia renamed and reframed: Intra-abdominal hypertension in pregnancy", Medical Hypotheses 83 (2014) 619-632.

Madanes AE, David D, Cetrulo C. "Major complications associated with intrauterine pressure monitoring." Obstet Gynecol, 1982;59:389-391.

Sugerman HJ., "Hypothesis: Preeclampsia is a venous disease secondary to an increased intra-abdominal pressure", Medical Hypotheses: 77 (2011)841-849.

Brent K. Lind, MD "Complications caused by extramembranous placement of intrauterine pressure catheters", Am J Obstet Gynecol 1999;180:1034-1035.

(Abstract Only) Devoe, LD, et al. "Monitoring intrauterine pressure during active labor. A prospective comparison of two methods", J Reprod Med. Oct. 1989; 34(10): 811-814.

(Abstract Only) Wilmink FA, et al., "Fetal complications after placement of an intrauterine pressure catheter: a report of two cases and review of the literature". J Maters Fetal Neonate Med 2008;21:880-883.

Rood, Kara M., et al."Use of Intrauterine Pressure Catheters (IUPPC) Increases Risk of Post-Cesarean Surgical Site Infection", Obstetric & Gynecology: May 2017, 129: 22 S.

Extended European Search Report dated Mar. 2, 2020 for European Application No. EP 19210264.8.

* cited by examiner

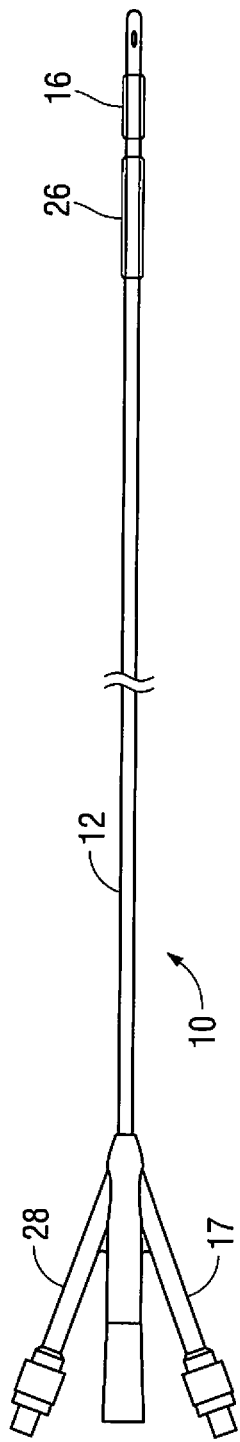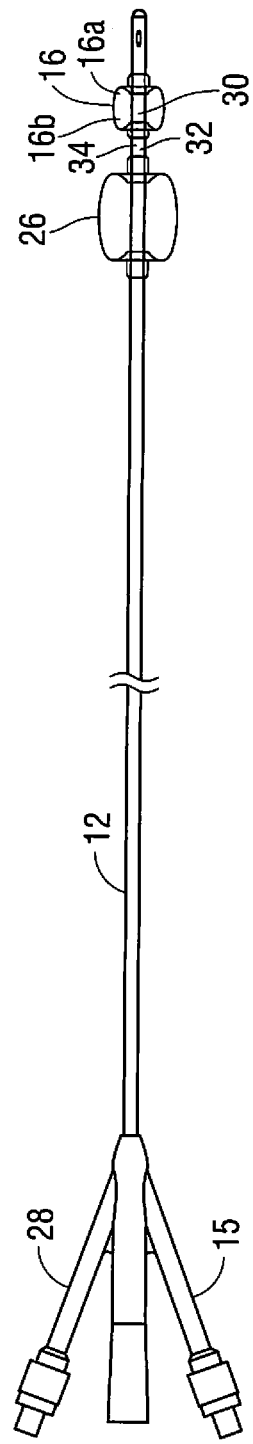
FIG. 1A
FIG. 1B

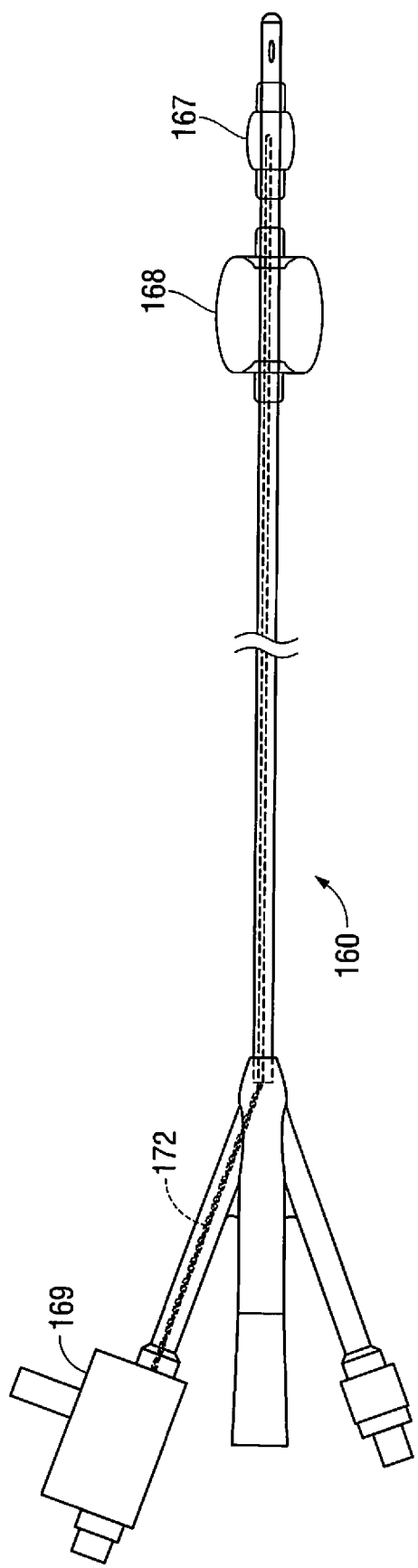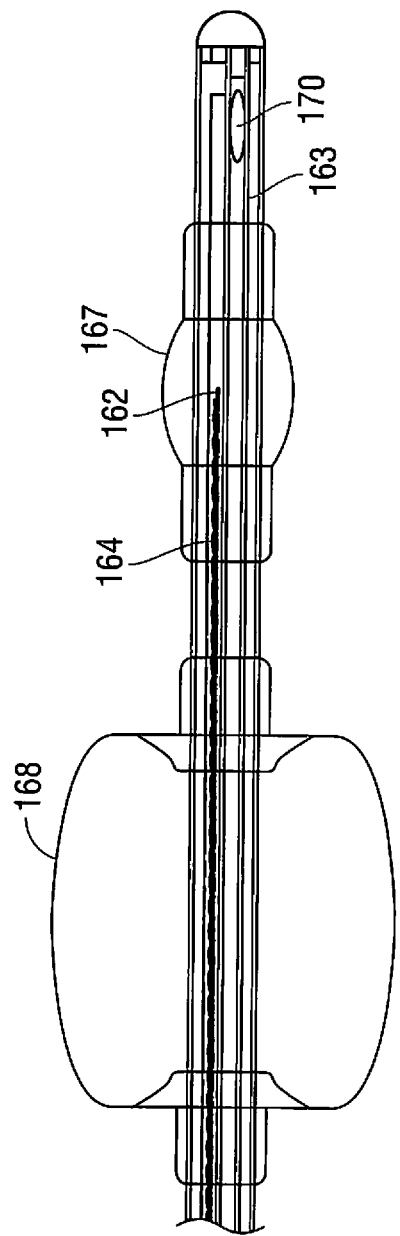
FIG. 14A
FIG. 14B

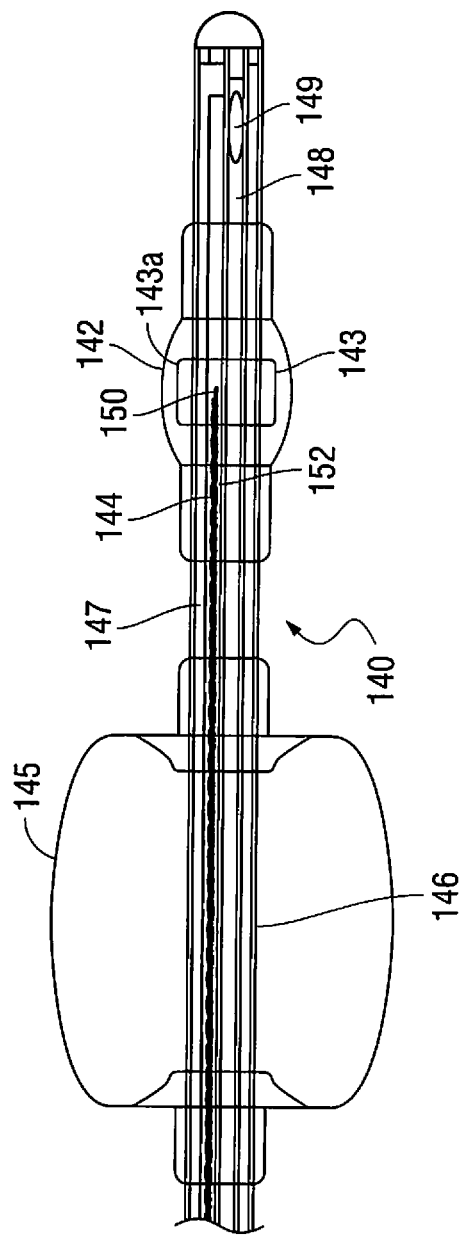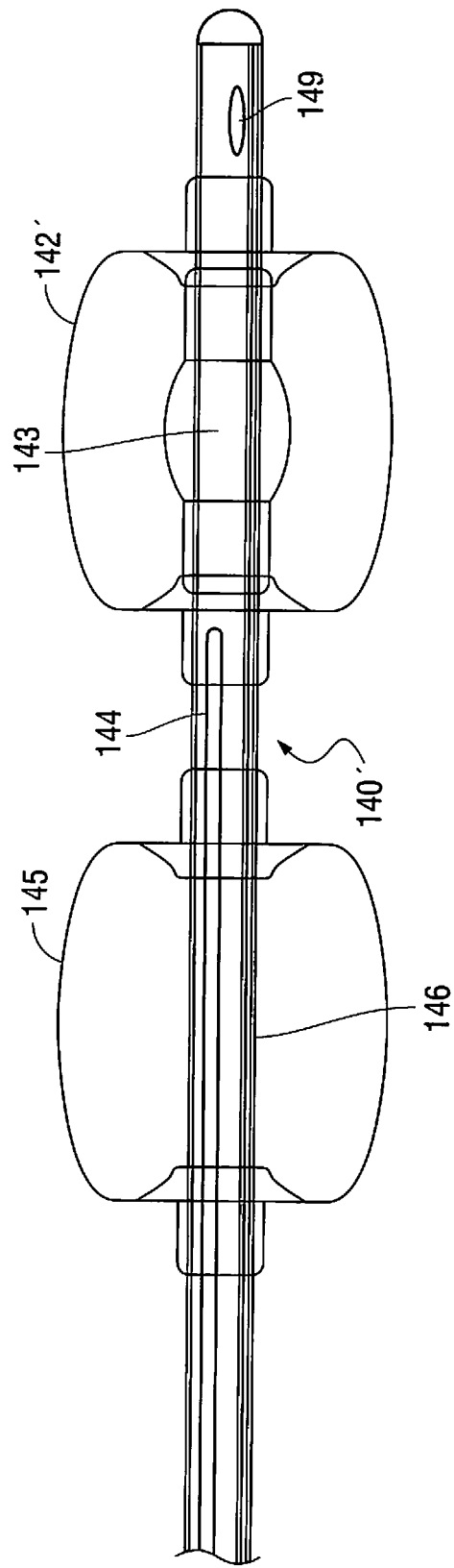
FIG. 15
FIG. 16

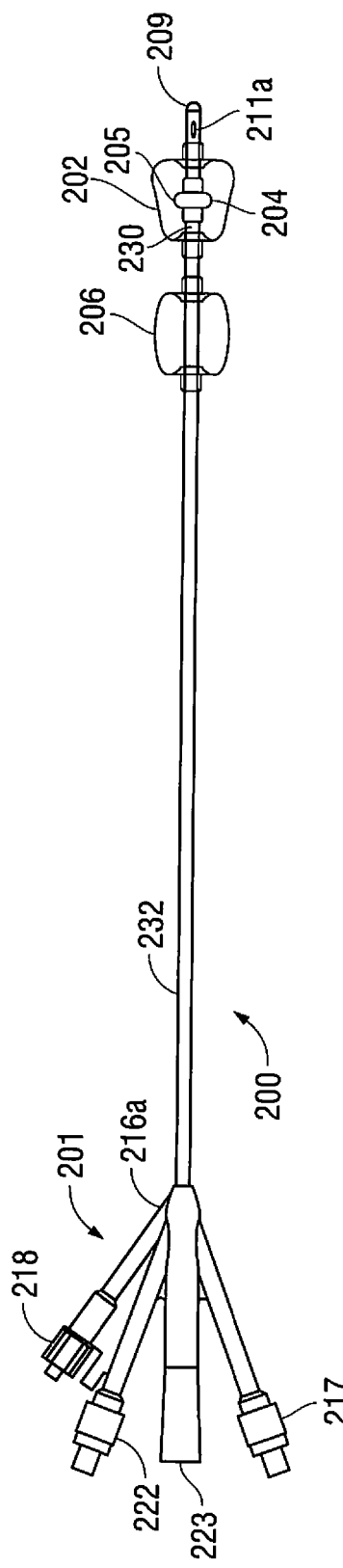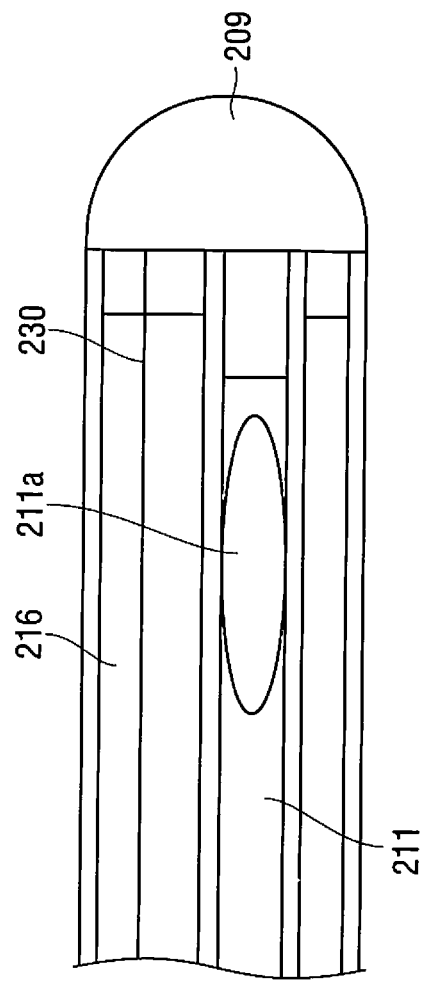
FIG. 18A
FIG. 18B

CATHETER FOR MONITORING UTERINE CONTRACTION PRESSURE

This application claims the benefit of provisional application Ser. No. 62/544,690, filed Aug. 11, 2017, provisional application Ser. No. 62/514,793, filed Jun. 3, 2017, provisional application Ser. No. 62/590,513, filed Nov. 24, 2017 and provisional application Ser. No. 62/622,871, filed Jan. 27, 2018. The entire contents of each of these applications are incorporated herein by reference.

BACKGROUND OF THE INVENTION

1. Field of the Invention

This application relates to a device and method for monitoring uterine contraction pressure through the urinary bladder.

2. Background

Traditionally, recording of uterine contraction has been performed through tocodynamometry, a strain gauge technology for measuring uterine contractions. The tocodynamometer is a transducer strapped onto the mother's abdomen in the area of the uterine fundus (typically around 10 cm above or below the umbilicus). This externally placed transducer has a tendency to become loose or fall off the maternal abdomen. Thus, it has to be periodically readjusted in order to record contractions. Also, this external transducer only measures the frequency and duration of the uterine contractions. Thus, it is limited since it does not measure the strength of uterine contraction pressure (UCP). Often accurate pressure measurement of uterine contraction is needed to determine adequacy of labor or the intensity of pre-term labor.

One product currently on the market available to accurately measure the UCP is the Intra-uterine Pressure Catheter (IUPC), a product offered by several large companies. The IUPC is placed in the uterus and measures the strength of the uterine contraction and makes a continuous recording on a bedside monitor. Labor induction or labor augmentation is utilized in about 20% of deliveries. Commonly during labor augmentation, the IUPC is needed to better quantify the intensity of uterine contractions, as explained in "Dystocia and Augmentation of Labor", ACOG Practice Bulletin, no. 49, Washington, D.C., American College of Obstetricians and Gynecologists, December 2003: 1445-54. The IUPC measures pressure by insertion of the catheter directly into the uterus. Original IUPCs used a column of water to measure pressure and required skilled personnel for setup. In the late 1980's, intra-uterine pressure catheters with an electronic sensor were developed which were easier to use and more accurate, as explained in "Monitoring Intrauterine Pressure During Active Labor. A Prospective Comparison of Two Methods", Devoe, L D. et al., J Reprod. Med. October 1989, 34(10):811-4. Shortly after, an IUPC with an air column to measure uterine contraction pressure was introduced. Thus, IUPCs currently employed measure uterine contraction pressure using various type of mechanisms such as a column of water, a column of air, or an electronic sensor.

While the monitoring of uterine contraction pressure using the foregoing devices is widely used and under proper circumstances can produce reliable measurements, there are a number of disadvantages associated with their use. Current IUPCs need to be inserted into the uterus through the cervix. The prerequisites for insertion of IUPCs are therefore: 1) the amniotic membrane has to be ruptured; 2) the cervix has to be dilated to allow the insertion of the IUPC; and 3) a trained medical personal is required to insert the IUPC. Another disadvantage of using current IUPCs is that they increase the risk of infection to the mother and baby. In an article, "Use of Intrauterine Pressure Catheter (IUPC) Increases Risk of Post-Cesarean Surgical Site Infection", Rood, Kara M., et al., Obstetrics & Gynecology: May 2017, 129:22.5, it was noted that laboring women undergoing cesarean delivery in whom the IUPC was used were at increased risk of post-cesarean surgical site infection. IUPC insertion can also cause severe complications such as placental abruption and anaphylactoid syndrome leading to maternal and/or fetal morbidity or death.

In addition to the traditional IUPC and the external tocodynamometry catheter, a device has been recently introduced on the market to measure the uterine contractions through detection of uterine electrical current. This method is called Electrohysterography (EHG). It has been shown by Euliano, et al. in "Monitoring Uterine Activity During Labor: A Comparison of 3 Methods", Am. J. Obstet, Gynec. January 2013 208 (1):66, 1-6, that EHG is a reliable non-invasive way to measure uterine contraction similar to the external tocodynamometry catheter. However, it is not able to quantitatively measure the force of the contraction. Another device being used is a disposable external tocodynamometry catheter by Clinical Innovations that utilizes an air charged system to measure contractions. Like the traditional external Tocodynamometry, this device is not able to quantify the force of the contractions.

It would be advantageous to provide a catheter that does not require the prerequisites described above for IUPCs, thus avoiding the need for the uterine cervix to be dilated or the amniotic membrane to be ruptured. It would also be advantageous if such uterine contraction pressure measuring catheters could measure core body temperature as well as drain urine from the bladder. There is also a need for such catheter to diminish the risks of infection to the mother or the baby associated with the prior and current use of IUPCs.

It would also be advantageous to provide a catheter capable of quantifying intensity of uterine contraction in non-laboring mothers and to accurately detect contraction in the mother with symptoms of preterm labor. Furthermore, it would be advantageous if such device could continuously measure pressure without interruption. This would advantageously enable a constant monitoring of uterine contraction pressure so critical time periods are not missed. It would further be advantageous to provide a device that improves the accuracy of the pressure reading to more accurately determine uterine contraction pressure.

Still further, it would be advantageous if such catheter could satisfy the foregoing needs and provide these above enumerated advantages while being simple to use so that any of the clinical staff with basic knowledge of bladder catheter insertion will be able to insert the device without relying on specially trained staff members, thereby reducing time and expense.

SUMMARY

It has been well known and validated that urinary bladder pressure directly correlates to intra-uterine pressure. Gravid uterus is an intra-abdominal organ in direct contact with the urinary bladder. Thus, the pressure generated by uterine contraction directly exerts pressure on the urinary bladder. Utilizing this correlation, the devices of the present invention measure bladder pressure to determine uterine contraction pressure (UCP), with measurement done in various ways, including the ways described in provisional application Ser. No. 62/514,793, filed Jun. 3, 2017, the entire contents of which are incorporated herein by reference.

The devices of the present invention do not require the insertion prerequisites described above for the current IUPC catheters, i.e., they do not require the uterine cervix to be dilated nor require rupture of the amniotic membranes.

The devices of the present invention can be easily inserted by the nurse, midwife, or a physician taking care of the laboring mother without requiring additional training or requiring a physician or trained staff skilled in insertion of the IUPC catheter. Since most mothers in active labor require a bladder catheter for drainage of urine, the catheters can be used to drain the bladder while also accurately measuring UCP without adding any risks to the mother or the baby. That is, the devices of the present invention can also drain urine from the bladder like ordinary bladder catheters.

The devices of the present invention in some embodiments are also able to measure core body temperature, fetal heart rate and/or maternal pulse oximetry (PO2).

The present invention therefore overcomes the deficiencies and disadvantages of the prior art. The present invention advantageously provides a multi-lumen catheter insertable into the bladder in the same manner as a regular bladder drainage catheter to determine uterine contraction pressure without requiring insertion of water into the bladder. The catheters of the present invention utilize a gas, e.g., air, charged chamber to measure bladder pressure across a large surface area, and thus, accurately determine uterine contraction pressure, and enable pressure to be measured continuously without interrupting urine flow and without interruptions to add water to the bladder.

Some embodiments of the catheter of the present invention utilize in addition to the pressure balloon a stabilizing balloon to help retain the catheter in the bladder during the procedure. These embodiments are discussed in more detail herein.

Various types of sensors are utilized with the several embodiments of the catheters of the present invention. For example, in some embodiments, the sensor measures both temperature and pressure; in other embodiments a separate sensor for measuring pressure and for measuring temperature are provided. Additionally, different locations for the sensors are disclosed. Each of these various embodiments is discussed in detail herein.

In accordance with one aspect of the present invention, a multi-lumen catheter for monitoring uterine contraction pressure is provided. The catheter comprises an elongated body configured and dimensioned for insertion into a bladder of a patient, the catheter having a first lumen, a second lumen, and a first balloon at a distal portion. The first lumen communicates with the first balloon and the second lumen communicates with the bladder to remove fluid from the bladder. The first balloon is filled with a gas to form along with the first lumen a gas filled chamber to monitor pressure within the bladder to thereby monitor uterine contraction pressure of the patient. A pressure sensor measures pressure about a circumferential area of the balloon, the pressure sensor continuously measuring pressure of the bladder to provide continuous readings of bladder pressure.

In accordance with another aspect of the present invention, a multi-lumen catheter for monitoring uterine contraction pressure is provided. The catheter comprises an elongated body configured and dimensioned for insertion into a bladder of a patient, the catheter having a first lumen, a second lumen, an outer balloon at a distal portion and an inner balloon within the outer balloon. The first lumen communicates with the inner balloon and the second lumen communicates with the bladder to remove fluid from the bladder, the inner balloon and first lumen filled with a gas to form a gas filled chamber to monitor pressure within the bladder to thereby monitor uterine contraction pressure of the patient. The outer balloon has a circumferential area greater than a circumferential area of the inner balloon and filled with a gas, e.g., air, wherein in response to pressure within the bladder exerted on an outer wall of the outer balloon, the outer balloon deforms and exerts a pressure on an outer wall of the inner balloon to deform the inner balloon and compress the gas within the inner balloon and the first lumen, the pressure sensor measuring bladder pressure based on gas compression caused by deformation of the inner balloon.

In accordance with another aspect of the present invention, a multi-lumen catheter for monitoring uterine contraction pressure is provided. The catheter comprises an expandable outer balloon at a distal portion of the catheter, an expandable inner balloon positioned within the outer balloon and a first lumen communicating with the inner balloon. The inner balloon and first lumen form a gas, e.g., air, filled chamber to monitor pressure within the bladder to thereby monitor uterine contraction of the patient, wherein the outer balloon has a circumferential area greater than a circumferential area of the inner balloon, wherein in response to pressure within the bladder exerted on the first outer wall of the expanded outer balloon, the outer balloon deforms and exerts a pressure on the second outer wall of the expanded inner balloon to deform the inner balloon and compress the gas within the inner balloon and the first lumen to provide a finer measurement. A second lumen communicates with the bladder to remove fluid from the bladder. An external pressure transducer is connectable to the catheter and communicates with the gas filled chamber for measuring bladder pressure based on gas compression caused by deformation of the expanded inner balloon deformed by the expanded outer balloon.

In accordance with another aspect of the present invention, a multi-lumen catheter for monitoring uterine contraction pressure is provided. The catheter comprises a distal balloon at a distal portion of the catheter and a first lumen communicating with the distal balloon. The distal balloon and first lumen form a gas, e.g., air, filled chamber to monitor pressure within the bladder to thereby monitor uterine contraction pressure of the patient, wherein in response to pressure within the bladder the distal balloon deforms to compress the gas within the distal balloon. The first lumen has a first proximal port communicating with the first lumen. A second lumen communicates with the bladder to remove fluid from the bladder. A temperature sensor is positioned in a third lumen of the catheter and has a wire extending through the third lumen. A hub is connectable to the first port of the catheter. The hub includes a pressure transducer for measuring pressure based on gas compression within the first lumen, wherein connection of the hub to the first port automatically connects the wire to an electrical connector in the hub for connection to a temperature monitor.

In accordance with another aspect of the present invention, a multi-lumen catheter for monitoring uterine contraction pressure is provided. The catheter comprises a distal balloon at a distal portion of the catheter and a first lumen communicating with the distal balloon. The distal balloon and first lumen form an air filled chamber to monitor pressure within the bladder to thereby monitor uterine contraction pressure of the patient, wherein in response to pressure within the bladder the distal balloon deforms to compress the air within the distal balloon. The first lumen has a first proximal port communicating with the first lumen. A second lumen communicates with the bladder to remove fluid from the bladder. A hub is connectable to the first port of the catheter, the hub including a pressure transducer for measuring pressure based on air compression with the first lumen. An elongated member extends distally from the hub, wherein connection of the hub to the first port automatically inserts the elongated member into the first lumen to advance air through the first lumen to expand the distal balloon, the first lumen not vented to atmosphere when the hub is connected to the first port.

In accordance with another aspect of the present invention, a method for measuring uterine contraction pressure is provided comprising the steps of a) providing a catheter having first and second lumens, an expandable first balloon, an expandable second balloon positioned over the first balloon, and a temperature sensor; b) inserting the catheter into a bladder of a patient; c) connecting a hub containing a pressure transducer to the catheter to automatically advance air through the first lumen of the catheter to expand the first balloon from a deflated condition to a more expanded condition; d) obtaining a first pressure reading of the bladder based on deformation of the first balloon caused by deformation of the second balloon in response to bladder pressure exerted on the second balloon; e) transmitting the first pressure reading to an external monitor connected to the hub, the first pressure reading providing an indicator of uterine contraction pressure; f) obtaining a second pressure reading of the bladder based on deformation of the first balloon caused by deformation of the second balloon in response to bladder pressure exerted on the second balloon; and g) transmitting the second pressure reading to the external monitor connected to the hub, the second pressure reading providing an indicator of uterine contraction pressure.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 1A is a side view of a first embodiment of the catheter of the present invention having a pressure balloon, a stabilizing balloon and a sensor positioned in the air lumen, both balloons shown in the deflated (collapsed) condition;

FIG. 1B is a side view similar to FIG. 1A showing the two balloons in the inflated (expanded) condition;

FIG. 14A is a side view of another alternate embodiment of the catheter of the present invention having dual pressure sensors, the first sensor positioned within the air lumen and the second sensor positioned external of the catheter, the two balloons shown in the inflated condition;

FIG. 14B is an enlarged view of the distal portion of the catheter of FIG. 14A;

FIG. 15 is a side view of another alternate embodiment of the catheter of the present invention having an outer and inner pressure balloon and a stabilizing balloon, the balloons shown in the inflated condition;

FIG. 16 is a side view similar to FIG. 15 illustrating an alternate embodiment having a larger outer balloon;

FIG. 18A is a side view of another alternate embodiment of the catheter of the present invention having a port for connection of an external pressure transducer and an outer and inner pressure balloon, the two balloons shown in the inflated condition;

FIG. 18B is close up view of the distal end of the catheter of FIG. 18A;

DETAILED DESCRIPTION OF PREFERRED EMBODIMENTS

Figure 2:
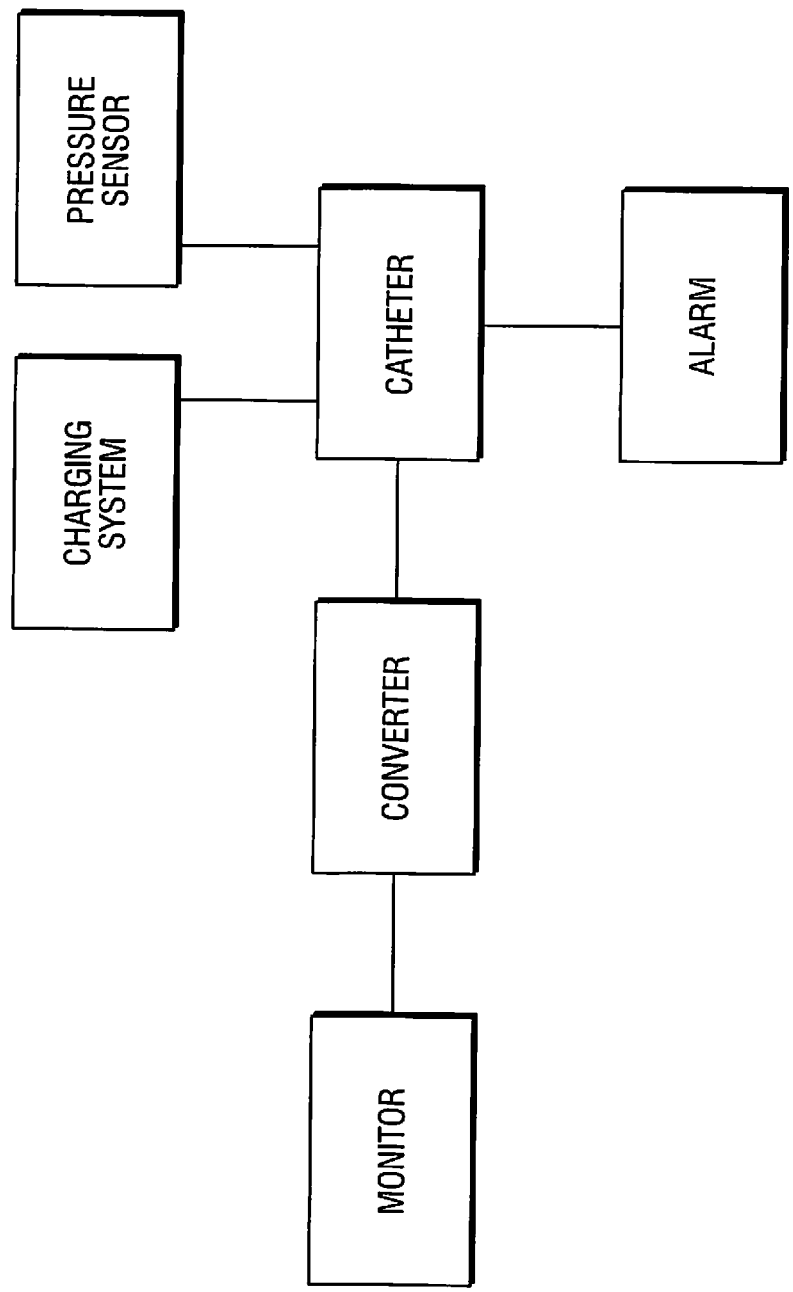
FIG. 2 is a schematic view of the system utilizing the catheter of FIG. 1A with an alarm system.

The catheters of the present invention are designed to continuously, safely, and accurately measure maternal uterine contraction pressure (UCP) and are inserted into the urinary bladder through the vaginal canal. In some embodiments, the catheters can also measure one or more of maternal core body temperature (CBT), maternal pulse and tissue oxygen saturation (PO2-partial pressure of oxygen), and fetal heart rate through the urinary bladder while continuously draining the bladder. These various features are discussed in detail below.

As noted above, the correlation between uterine contraction pressure and urinary bladder pressure directly is known. Gravid uterus is an intra-abdominal organ in direct contact with the urinary bladder. That is, the pressure generated by uterine contraction directly exerts pressure on the urinary bladder. The catheters of the present invention utilize this correlation to effectively measure uterine contraction pressure.

Furthermore, in some embodiments, the catheter of the pressure invention provides a dual sensor to provide a backup pressure reading. In other embodiments a dual pressure balloon arrangement is provided. These various embodiments are discussed in more detail below.

Referring now to the drawings and particular embodiments of the present invention wherein like reference numerals identify similar structural features of the devices disclosed herein, there is illustrated in FIGS. 1-5 a catheter of a first embodiment of the present invention. The catheter (device) is designated generally by reference numeral 10 and is configured for insertion into and positioning within the bladder of the patient for measuring uterine contraction pressure. The catheter can be connected to a bedside or central monitor through a wired or blue tooth wireless connection to display continuous readings of the maternal and fetal vitals.

The catheter 10 of the present invention can in some embodiments include an alarm or indicator to alert the user if pressure rises beyond a threshold or predetermined value (pressure). The indicator or alarm can be on the catheter or alternatively on an external device such as the monitor as discussed in more detail below. The alarm can also be connected via wireless connection to a phone or remote device to alert the appropriate personnel. The alarm can alternatively or in addition be activated if a change in pressure measurement exceeds a specified rate over a specified period of time. The alarm can also be triggered by other parameters, e.g., excessive temperature, oxygen levels, fetal heart rate, etc. in embodiments that have sensors for detection of these parameters.

Turning now to details of the catheter 10, which is also referred to herein as the device 10, and with initial reference to FIGS. 1A, 1B, 3 and 4, the three-lumen catheter 10 has an elongated flexible shaft 12 having a lumen (channel) 14 extending within the shaft 12 and communicating at its distal region with balloon 16 to fluidly communicate with balloon 16 to inflate the balloon. Balloon 16 is utilized for monitoring pressure and is also referred to herein as the "pressure balloon." A fluid port 15 is positioned at a proximal region 17 of the catheter 10 for communication with an infusion source for infusion of gas, e.g., air, through the lumen 14 and into the balloon 16. The catheter 10 is shown in FIG. 1A with balloon 16 in the deflated condition (position) and in FIG. 1B with the balloon 16 in the inflated condition (position). The shaft 12 also includes a second lumen (channel) 20 and third lumen (channel) 24 extending therein (see also FIG. 5). In a preferred embodiment, the second lumen 20 is the largest lumen and is configured for continuous drainage of bodily contents from the bladder and can be connected to a drainage bag for collection of urine. Second lumen has a side opening 22 at a distal portion, best shown in FIG. 3, communicating with the bladder. The third lumen 24 terminates at its distal end within balloon 26 to fluidly communicate with balloon 26 to inflate the balloon 26. The balloon 26 is inflatable to stabilize the catheter 10 to limit movement of the catheter 10 to keep it in place within the bladder and is also referred to herein as "the stabilizing balloon" or "retention balloon." A fluid port 28 is positioned at a proximal region 17 of the catheter 10 for communication with an infusion source for infusion of fluid through the lumen 24 and into the balloon 26. The balloon 26 can be filled with fluid, e.g., liquid such as water or saline, or a gas, e.g., air. In FIG. 1A, the balloon 26 is shown in the deflated condition and in FIG. 1B in the inflated condition.

Figure 5:
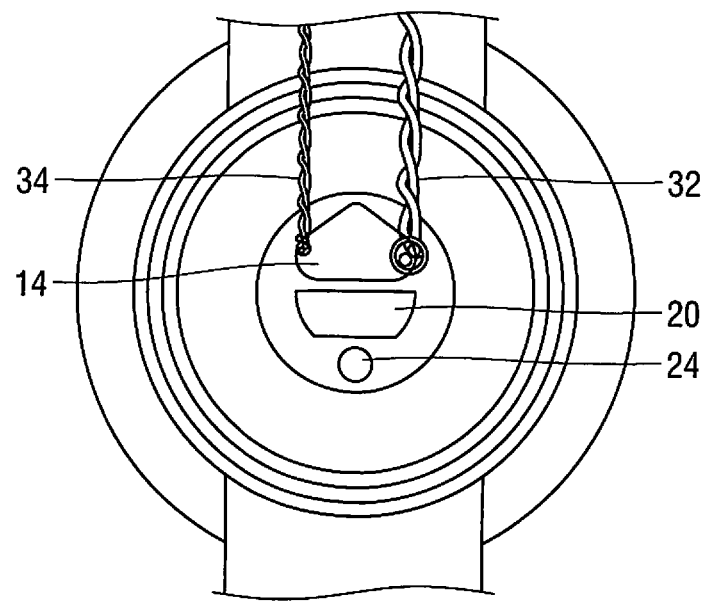
FIG. 5 is an enlarged transverse cross-sectional view of the catheter of FIG. 1A.
Figure 6:
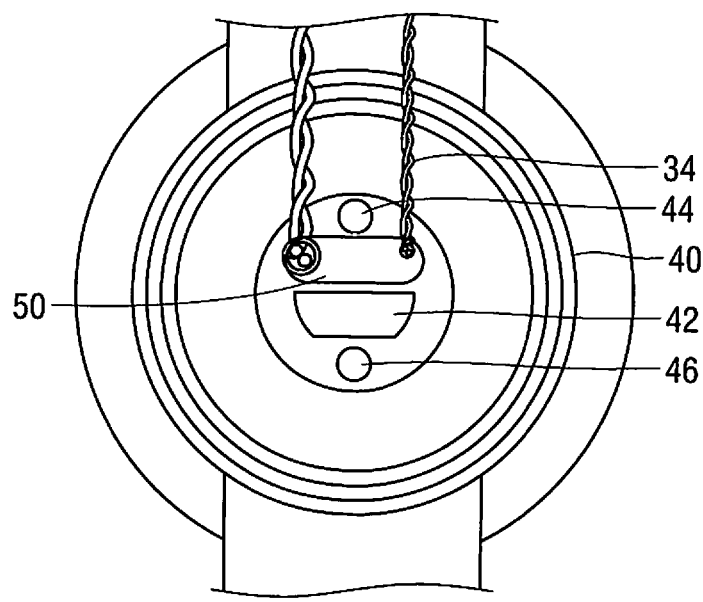
FIG. 6 is an enlarged transverse cross-sectional view of an alternate embodiment of a catheter of the present invention having four lumens.
Figure 10A:
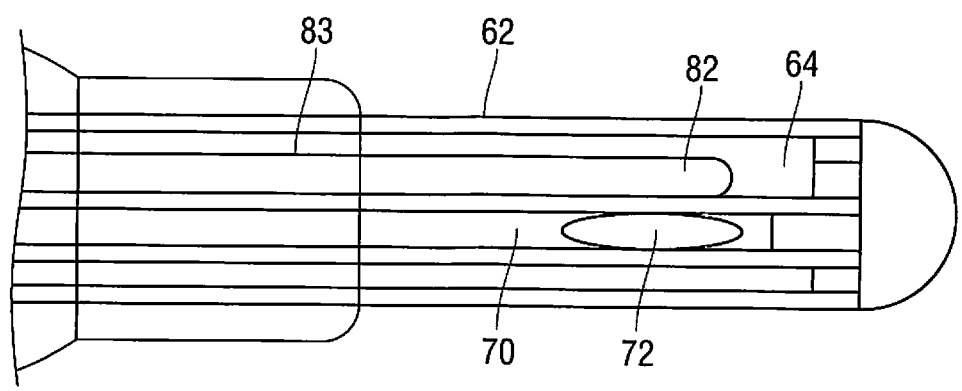
FIG. 10A is a close up view of the distal portion of the catheter of FIG. 8A.
Figure 10B:
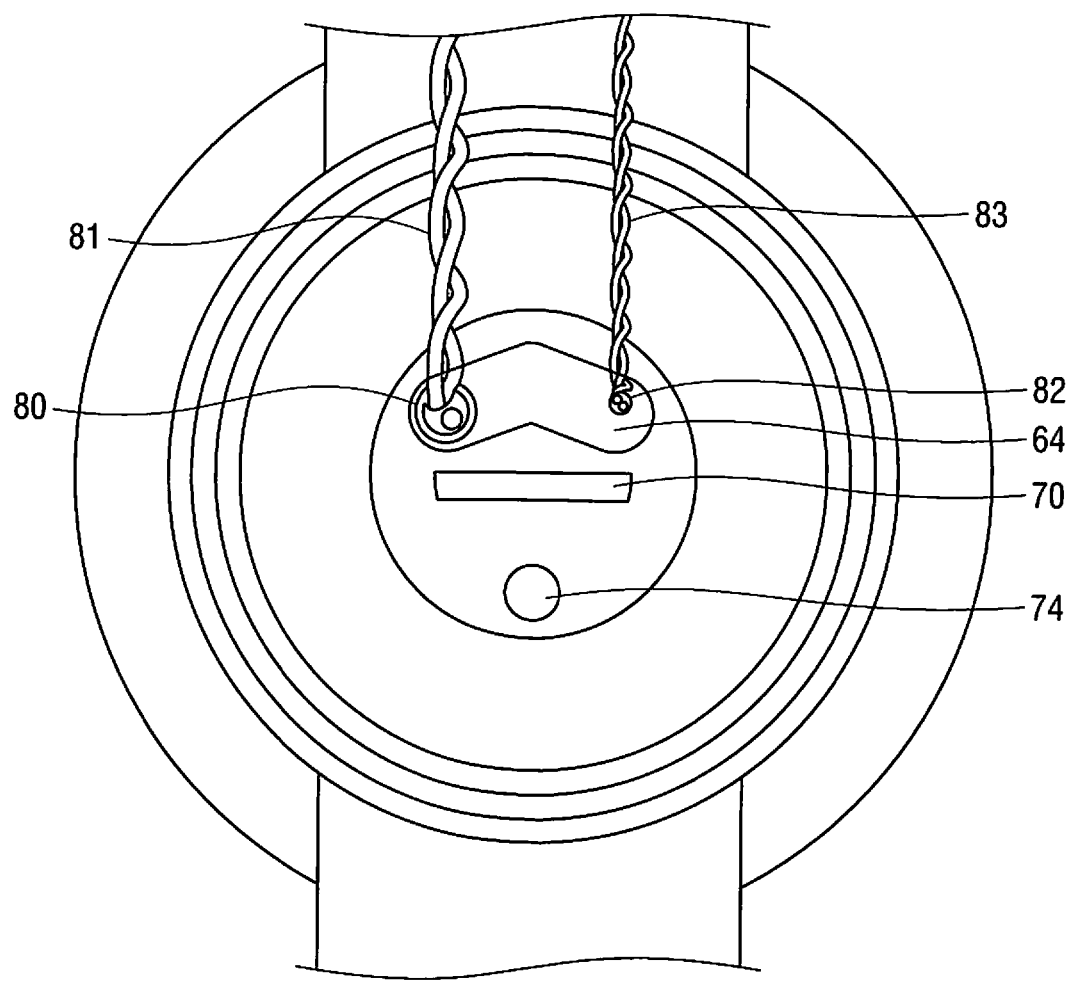
FIG. 10B is an enlarged transverse cross-sectional view of the catheter of FIG. 8A.

Note FIG. 5 is a transverse cross-section of the catheter showing the three lumens of various shapes. These cross-sectional shapes of the lumens are provided by way of example as one or more of the lumens can be circular, oval or other symmetrical or asymmetrical shapes in transverse cross section. This also applies to the cross-sectional views of the other embodiments herein, e.g., FIGS. 6, 10B and 23, wherein the lumens can be shapes other than those shown. As noted above, preferably the drainage lumen is the largest lumen but in alternate embodiments one or more of the other lumens could be larger than the drainage lumen.

A sensor 30 is positioned within lumen 14 adjacent balloon 16. The wire(s) 32 are shown extending through lumen 14, the sensor 30 and wire(s) 32 being of sufficiently small size so as not to interfere with air flow though lumen 14. The sensor 30 measures pressure of the bladder. The sensor 30 is part of a transducer for converting the variation in pressure to an electrical signal for transmission to an external monitor. The pressure sensor also includes a temperature sensor to measure core temperature of the body as seen inside the bladder. Transmission wire(s) 34 of the temperature sensor extend adjacent wire 32 through lumen 14 and terminate external of the catheter 10 for connection to an external monitor. The transducer can be wired directly to the monitor or alternatively wired to a converter external of the catheter for converting the signal received by the transducer and transmitting a signal to the monitor, e.g., a bedside monitor, to display the pressure readings. This is shown schematically in FIG. 2. The readings can be displayed in quantitative form, graphical form or other displays to provide an indicator to the clinician of the bladder pressure. The monitor, or a separate monitor, will display the temperature readings from sensor 30. Alternatively, the sensor/transducer can be connected to the monitor via a Bluetooth wireless connection.

Wires 32 and 34 can extend though lumen 14 and exit side port 15 for connection to a converter or monitor or alternatively can be inserted through the lumen 14, piercing the wall to enter the lumen 14 distal of the side port.

An alarm system can also be provided wherein the system includes a comparator for comparing the measured pressure (and/or temperature) to a threshold (predetermined) value, and if such threshold is exceeded, an indicator, e.g., an alarm, is triggered to indicate to the hospital personnel the excessive pressure and/or temperature. An alarm system can alternatively or in addition be activated if a change in pressure measurement exceeds a specified rate over a specified period of time. This would alert the staff to an imminent risk of pressure exceeding a certain value.

The alarm system can be part of the catheter (as shown in FIG. 2) or alternatively external to the catheter 10.

In the embodiments wherein other parameters are measured, the alarm system described herein can be tied into measurement of these parameters. For example, an alarm can be triggered if the fetal heart rate is outside predetermined levels, if oxygen levels are outside predetermined levels, if maternal core body temperature is outside core body levels, etc.

The lumen 14 and space 16a within balloon 16 together form a closed air chamber, i.e., the lumen 14 forming an air column. With the balloon 16 filled with air, pressure on the external wall of the balloon will force the balloon to deform inwardly, thereby compressing the air contained within the balloon space 16a and within the lumen 14. The pressure sensor 30 is located in a distal portion of the lumen 14 at the region of the balloon 16 and thus is positioned at the distal end of the air column. Therefore, the pressure is sensed at the distal region as the sensor 30 detects change in air pressure in lumen 14 due to balloon deformation. Placement of the sensor 30 at a distal location provides a pressure reading closer to the source which in some applications can increase the accuracy by reducing the risk of transmission issues by reducing the amount of interference which could occur due to water, air, clots, tissue, etc. if the transmission is down the air lumen (air column).

Additionally, the pressure measurement occurs about a more circumferential area of the balloon 16 providing a pressure reading of a region greater than a point pressure sensor reading. Also, average pressure over an area of the bladder wall can be computed. Thus, the area reading gleans information on pressure over more of the bladder wall. Stated another way, the balloon has a relatively large surface area with multiple reference points to contribute to average pressure readings of the surface around it by the sensor.

The air column is charged by insertion of air through the side port 15 which communicates with lumen 14. The side port 15 includes a valve to provide a seal to prevent escape of air from a proximal end. The balloon 16 can be composed of impermeable material, or in alternative embodiments, a permeable or semi-permeable material with an impermeable coating. This seals the air column at the distal end to prevent escape of air through the distal end, i.e., through the wall of the balloon 16. Thus, with the lumen sealed at the proximal and distal ends, a closed air system (air charged system) is provided, and without the requirement for repeated water insertion into the bladder, a fully closed unit is provided.

In preferred embodiments, when the lumen 14 is air charged, the balloon 16 is not fully inflated. This improves the accuracy of the balloon 16 transmitting pressure from external the balloon to the interior of the balloon and into the lumen, i.e., air column, by ensuring the balloon has sufficient compliancy to prevent the balloon from introducing artifact into the pressure reading which would diminish its accuracy.

In some embodiments, the pressure balloon 16 is of a size to receive at least about 3 cc (3 ml) of fluid. However, other sizes/volumes are also contemplated such as about 2 cc or about 1 cc. Additionally, these volumes represent the maximum volume of fluid for the balloon, however, as noted above, in preferred embodiments, the pressure balloon 16 is not fully inflated so it would receive less than the maximum volume. Thus, with a balloon of X volume, the fluid would receive X-Y fluid, with Y representing the amount of desired extra space to achieved desired compliancy of the balloon while still enable sufficient inflation of the balloon to achieve its pressure induced deformation function.

Note in this embodiment, the stabilizing balloon 26, also referred to as the proximal retention balloon, is positioned proximal of the pressure balloon 16. Also, in this embodiment, the stabilizing balloon 26 is larger than the pressure balloon 16. By way of example, the stabilizing balloon 26 can have a fully expanded diameter of about 23 mm and the pressure balloon 16 can have a fully expanded diameter of about 15 mm, although other dimensions or diameters for these balloons are also contemplated. By way of example, the stabilizing balloon 26 can have a capacity of about 10 cc (10 ml) of air, although other sizes/volumes are also contemplated. Note these sizes/volumes for both balloons are provided by way of example and other sizes are also contemplated. Alternatively, the stabilizing balloon can be the same size or smaller than the pressure balloon. Various shapes of the balloons are also contemplated.

Additionally, although the balloon 26 is positioned proximal of the balloon 16, it is also contemplated that the balloon 26 be positioned distal of balloon 16. The axial spacing of the balloons 16, 26 enable the stabilizing balloon 26 to engage the bladder wall to provide a sufficient radial force thereon for securing/mounting the catheter within the bladder without interfering with the function of balloon 16.

Figure 3:
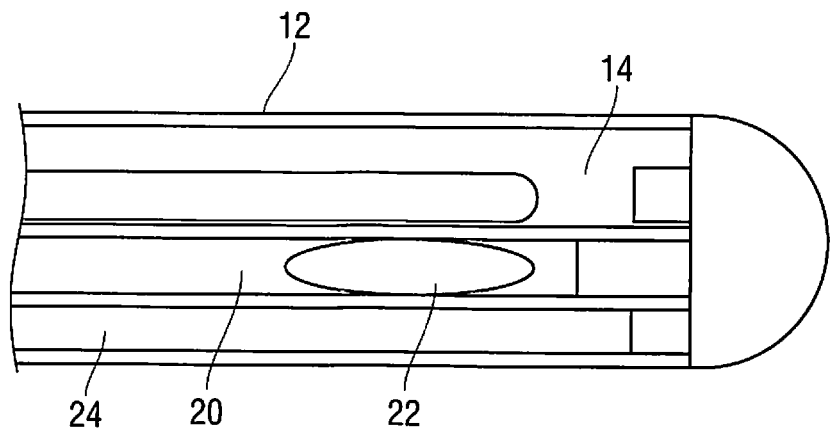
FIG. 3 is a close-up view of the tip of the catheter of FIG. 1A.
Figure 4:
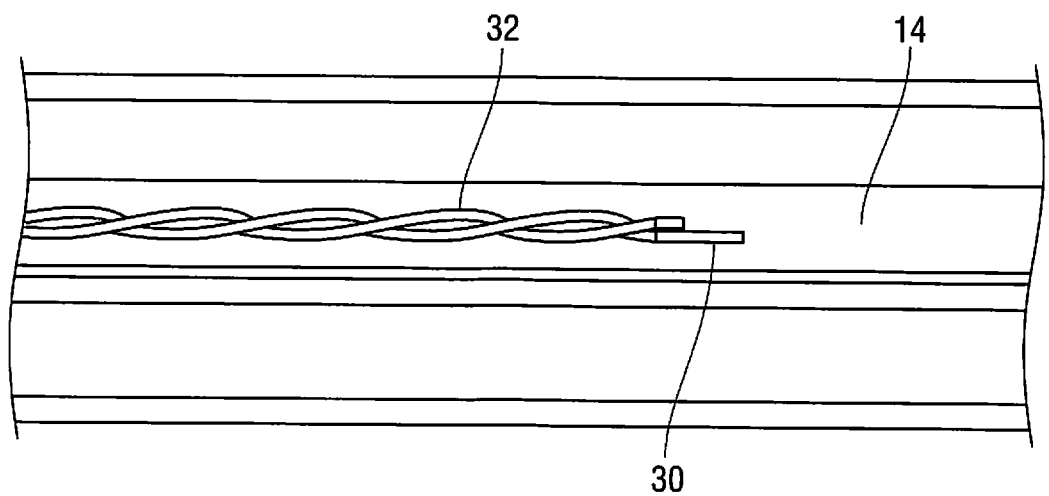
FIG. 4 is a close-up view of the sensor of FIG. 1 within the air lumen.
Figure 7:
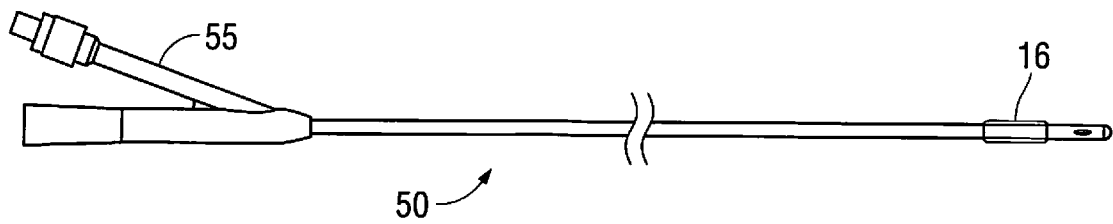
FIG. 7 is a side view of an alternate embodiment of the catheter of the present invention similar to FIG. 1 except having a single balloon, the balloon shown in the inflated condition.

It should be appreciated that although the stabilizing balloon is shown in the embodiment of FIG. 1, it is also contemplated as an alternative, the catheter and system of FIGS. 1 and 2 can be utilized without the stabilizing balloon 26 as shown for example in FIG. 7. Similarly, although the various embodiments (catheters) disclosed herein utilize a stabilizing balloon, it is also contemplated that alternatively the catheter of these various embodiments not include a stabilizing balloon. In the embodiment of FIG. 7, catheter 50 has two lumens: 1) a lumen for continuous drainage of the bladder which has a side opening at a distal end to communicate with the bladder (similar to lumen 20 of FIG. 1); and 2) an air lumen filling pressure balloon 16 via insertion of air through side port 55. The sensor 30 is positioned within the air lumen in the same manner as sensor 30 is in lumen 14 or in the alternative positions disclosed herein. Thus, the pressure and temperature sensing described in conjunction with FIG. 1A is fully applicable to the embodiment of FIG. 7. Besides the elimination of the stabilizing balloon and its lumen and side port, catheter 50 is the same as catheter 10, Note that although only one sensor is shown in FIG. 3, it is also contemplated that multiple sensors can be provided. Also, note that the sensor 30 is positioned in lumen 14 at a mid-portion of the balloon, i.e., just proximal where the opening in lumen 14 communicates with the interior 16a of the balloon 16. It is also contemplated that the sensor can be placed at another portion within the lumen 14, e.g., a more proximal portion, with respect to the lumen opening. Also, the lumen opening need not be at the mid portion of the balloon and can be at other regions of the balloon to communicate with the interior space 16a. Note if multiple sensors are provided, they can be positioned at various locations within the lumen 14.

As shown, the sensor 30 and its transmission wires are located in the same lumen 14 also used for initial inflation gas, e.g., air, for balloon 16 and for the air charged column. This minimizes the overall transverse cross-section (e.g., diameter) of the catheter 10 by minimizing the number of lumens since additional lumens require additional wall space of the catheter. However, it is also contemplated in alternate embodiments that the sensor is in a dedicated lumen separate from the inflation lumen 14. This can be useful if a larger sensor or additional wires are utilized which would restrict the air lumen if provided therein. This is also useful if a specific sized lumen for the sensor and wires is desired to be different than the sized lumen for the air column. Provision of a separate lumen is shown in the cross-sectional view of FIG. 6 wherein in this alternate embodiment catheter 40 has four lumens: 1) lumen 42 for drainage of the bladder which has a side opening at a distal end to communicate with the bladder (similar to lumen 20 of FIG. 1); 2) lumen 44 for filling pressure balloon 16; 3) lumen 46 for filling stabilizing balloon 26; and 4) lumen 50 in which sensor 30 and its transmission wires 32 and temperature sensor wires 34 are contained. In all other respects, catheter 40 is identical to catheter 10 and its balloons, air channel, sensor, etc. would perform the same function as catheter 10. Therefore, for brevity, further details of catheter 40 are not discussed herein as the discussion of catheter 10 and its components and function are fully applicable to the catheter 40 of the embodiment of FIG. 6.

Turning now to the use of the catheter 10, the catheter 10 is inserted into the bladder. Note catheter 50 (and catheter 40) would be used in the same manner. The balloon 26 is inflated to secure the catheter 10 in place during the procedure by insertion of a fluid (liquid or gas) through side port 28 which is in fluid communication with lumen 24. The system is charged by inflation of the balloon 16, i.e., preferably partial inflation for the reasons discussed above, by insertion of air via a syringe or other inflation device through port 15 which is in fluid communication with lumen 14. As discussed above, the catheter 10 is a closed system with the pressure balloon 16 sealed so that air inserted through lumen 14 and into balloon 16 cannot escape through balloon 16. Thus, a closed chamber is formed comprising the internal space 16a of the balloon 16 and the internal lumen 14 communicating with the internal space 16a of balloon 16. With the balloon 16 inflated, pressure monitoring can commence. When external pressure is applied to an outer surface 16b of the balloon 16, caused by outward uterine pressure which applies pressure to the bladder wall and thus against the wall of balloon 16, the gas within the chamber is compressed. The sensor 30 at the distal end of lumen 14 provides continuous pressure readings, converted to an electrical signal by the transducer within the distal end of lumen 14, and then electrically communicates through wire(s) 32 extending through lumen 14, exiting through the proximal side port 15 and connected to an external monitor 44. Note the wire can terminate at the proximal end in a plug in connector which can be connected directly to the monitor or alternatively plugged into a converter to convert the signals from the transducer in the embodiments wherein the converter is interposed between the wires and monitor (see e.g., the system of FIG. 2) to provide the aforedescribed graphic display. Although, the system is capable of continuous pressure and temperature monitoring, it can also be adapted if desired for periodic monitoring so the pressure and/or temperature readings can be taken at intervals or on demand by the clinician.

In the embodiments wherein an indicator is provided, if the measured pressure exceeds a threshold value, and/or a change in pressure measurement exceeds a specific rate over a specific time period, the indicator would alert the clinician, e.g., via a visual indication or an audible indication, that the threshold is exceeded. The indicator in some embodiments can include an audible or visual alarm (shown schematically in FIG. 2). In the embodiments having an indicator, the indicator can be provided on a proximal end of the catheter which extends out of the patient or the indicator can be part of an external component such as the monitor or a separate alarm system. A visual, audible, or other indicator can likewise be provided in any of the other embodiments disclosed herein to indicate if the measured pressure, measured temperature or any other measured parameter exceeds a predetermined value, and such indicator can include an alarm and can be part of the catheter or a separate component.

The catheter 10 can be positioned in close proximity to the fetus and thus can include one or more pressure sensors in an additional channel (lumen) of the catheter to detect fetal heart rate. The catheter can also include a channel (lumen) with one or more sensors to detect continuous maternal PO2. Such additional sensor(s) can be provided in any of the catheters disclosed herein. Thus, in some embodiments, the catheter 10 (as well as the other catheters disclosed herein) can measure intrauterine pressure along with measurement or detection, either continuously or intermittently, of one or more of the following; 1) maternal core body temperature; 2) maternal respiration; 3) maternal PO2; and 4) fetal heart rate. This is in addition to continuous drainage of bodily contents from the bladder. One way for example to measure fetal heart rate is to place a micro air charged chamber in the retention balloon to help detect fetal heart rate. Sensors can be provided to detect continuous maternal PO2 located near the urethra, proximal to the stabilizing balloon.

Figure 8A:
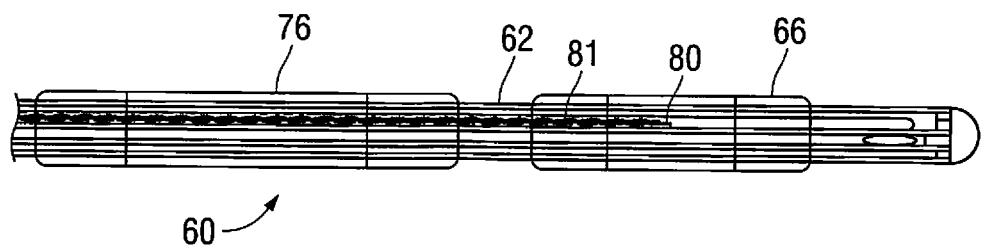
FIGS. 8A and 8B are side views of an alternate embodiment of the catheter of the present invention having two balloons and a pressure sensor and a separate temperature sensor in the air lumen, the two balloons shown in the deflated condition, with FIG. 8A showing the distal end and FIG. 8B showing the proximal end of the catheter.

In the embodiment of FIGS. 1-7, within the distal end of the air lumen 14 is a pressure transducer and pressure sensor 30 which also includes a temperature sensor. In the alternate embodiment of FIGS. 8A-10B, the temperature sensor is separate from the pressure sensor. More specifically, catheter 60 has an elongated flexible shaft 62 having a lumen (channel) 64 extending within the shaft 62 and fluidly communicating at a distal region with balloon 66 to inflate the balloon. Balloon 66 (also referred to as the pressure balloon) is utilized for monitoring pressure. A fluid side port 65 is positioned at a proximal region 67 of the catheter 60 for communication with an infusion source for infusion of gas e.g., air, through the lumen 64 and into the balloon 66. The catheter 60 is shown in FIG. 8A with balloon 66 in the deflated condition (position) and in FIG. 9 with the balloon 66 in the inflated condition (position). The shaft 62 also includes a second lumen (channel) 70 and third lumen (channel) 74 extending therein. The second lumen 70 is preferably the largest lumen and is configured for drainage of the bladder. Second lumen 70 has a side opening 72 at a distal portion communicating with the bladder. The third lumen 74 communicates at a distal region with stabilizing (retention) balloon 76 to fluidly communicate with balloon 76 to inflate the balloon. The stabilizing balloon 76 is inflatable to stabilize the catheter 60 to limit movement of the catheter 60 to keep it in place within the bladder. A side fluid port 75 is positioned at a proximal region 67 of the catheter 60 for communication with an infusion source for infusion of fluid through the lumen 74 and into the balloon 76.

Figure 9:
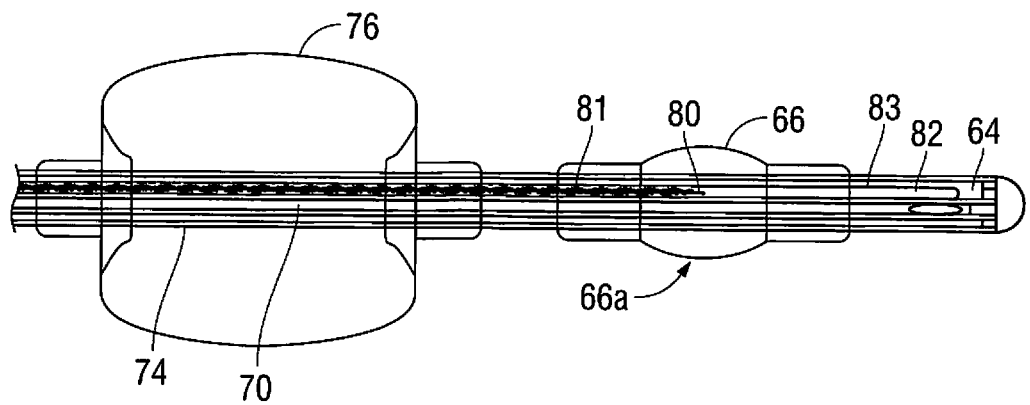
FIG. 9 is a side view similar to FIG. 8A showing the two balloons in the inflated condition.

Sensor 80 is positioned in lumen 64 for sensing pressure in response to balloon deformation in the same manner as sensor 30. Sensor 82 is positioned in lumen 64 distal of sensor 80 for measuring maternal core body temperature. Temperature sensor 82 can be a thermocouple, a thermistor or other types of temperature sensors. As shown in FIG. 9, the temperature sensor is distal of the balloon 66 and its transmission wire(s) 83 extend proximally within lumen 64, exiting a proximal end for communication with a monitor or alternatively a converter which communicates with the monitor. Wire(s) 81 of sensor 80 also extend through lumen 64, alongside wire(s) 83, exiting through the side port 65 or a proximal end wall or a side wall of the lumen. It is also contemplated that alternatively one or both of sensors 80 and 82, and their associated wires 81, 83, can be positioned in a separate "fourth" lumen such as in the embodiment of FIG. 6 so that the "inflation lumen" and the "sensor lumen" are independent.

In use, catheter 60 is inserted into the bladder and stabilizing balloon 76 is inflated to secure the catheter 60 in place. The system is charged by inflation of the balloon 66, i.e., preferably partially inflated for the reasons discussed above, by insertion of air (or other gas) through port 65 which is in fluid communication with lumen 64 in a closed system formed by the internal space 66a of the balloon 66 and the internal lumen 64 communicating with the internal space 66a of balloon 66. With the balloon 66 inflated, pressure monitoring can commence as external pressure applied to an outer surface of the balloon 66 compresses the gas within the chamber. The sensor 80 at the distal end of lumen 64 provides continuous pressure readings, converted to an electrical signal by the transducer within the distal end of lumen, and then electrically communicates through wires 82 extending through lumen 64 to an external monitor either directly or via a converter. The sensor 82 at the distal end of lumen 64 provides continuous temperature readings via wires 83 communicating directly or indirectly with the monitor, Although, the system is capable of continuous pressure and continuous temperature monitoring, it can also be adapted if desired for periodic monitoring so the pressure and/or temperature readings can be taken at intervals or on demand by the clinician. If provided, measurements of other parameters discussed above and in the various embodiments disclosure herein can also be taken continuously or at intervals.

Figure 8B:
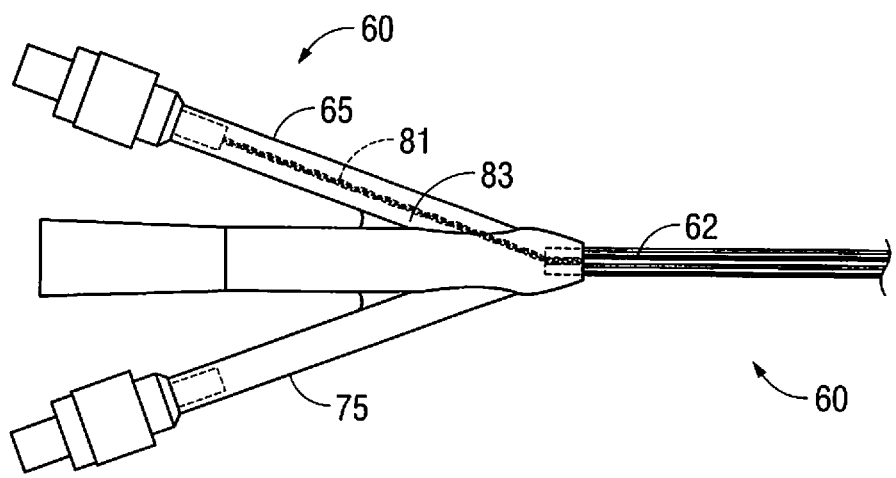
Figure 11:
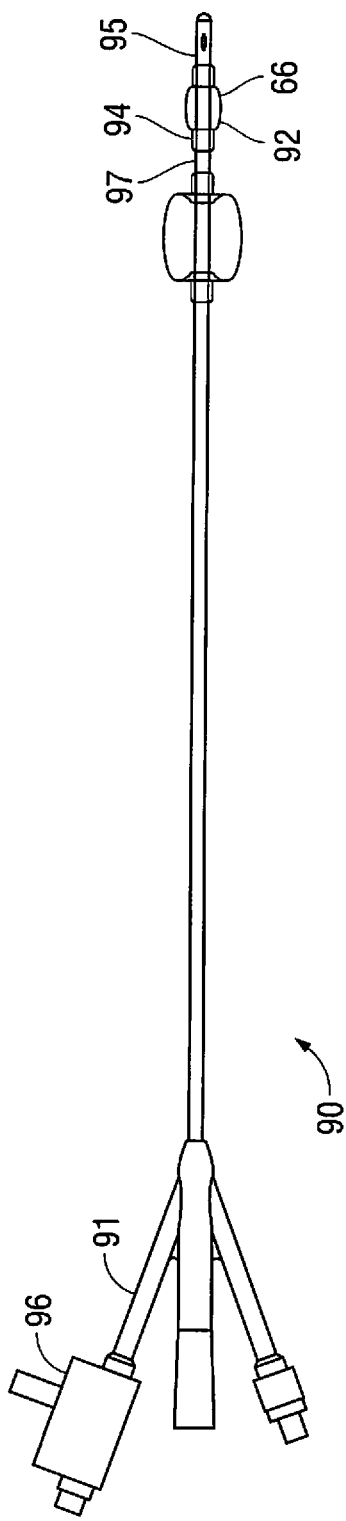
FIG. 11 is a side view of another alternate embodiment of the catheter of the present invention having two balloons, a sensor in the air lumen and an external transducer, the two balloons shown in the inflated condition.

In the alternate embodiment of FIG. 11, catheter 90 is identical to the catheter 60 of FIG. 8 except that the pressure transducer is positioned external of the catheter rather than in the air (or other gas) lumen. That is, instead of the pressure transducer including the sensor being positioned within the distal end of the air lumen, the pressure sensor 92 is positioned within lumen 94 at the distal end of the lumen and transmission wire(s) 93 connect the sensor 92 to the pressure transducer 96 positioned outside of the patient at a proximal region of catheter 90. As shown, the pressure transducer 90 can be positioned in a side port of catheter 90. In alternate embodiments, it is positioned outside the catheter. The temperature sensor 95 is positioned within lumen 94 along with transmission wire (97) in the same manner as temperature 82 and wires 83 are positioned in catheter 60 described above. The temperature sensor can be a separate sensor positioned distal of the pressure sensor 92 as shown or alternatively it can be part of sensor 92 as in the embodiment of FIG. 1. In all other respects, catheter 90 is identical to catheter 60 and therefore for brevity further discussion is not provided since the structure and function of the balloons, the lumens, the positioning of the sensors in the lumens, the continuous pressure monitoring, etc., as well as the aforedescribed alternative arrangements of catheter 60, are fully applicable to the catheter 90.

Figure 12:
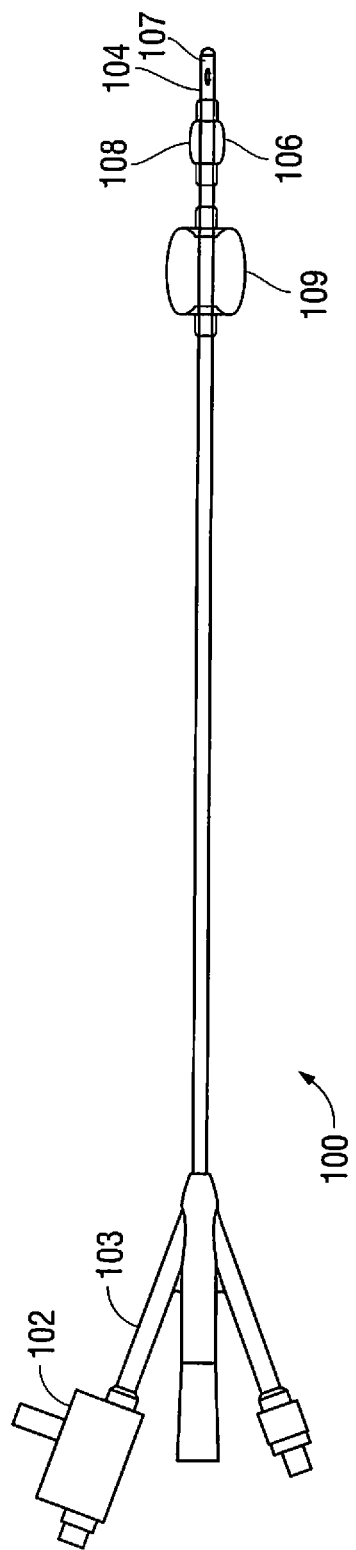
FIG. 12 is a side view of another alternate embodiment of the catheter of the present invention having two balloons, a temperature sensor in the air lumen and the pressure sensor external of the catheter, the two balloons shown in the inflated condition.

In the alternate embodiment of FIG. 12, catheter 100 is identical to catheter 60 of FIG. 8 except that both the pressure transducer and the pressure sensor are positioned external of the patient at a proximal region of the catheter rather than in the air lumen. That is, instead of the pressure transducer and sensor being positioned within and at the distal end of the air lumen, the transducer and pressure sensor 102 are positioned in a side port 103 of the catheter 100. In alternative embodiments, they are positioned outside the catheter. In yet other embodiments, the pressure sensor and/or pressure transducer can be positioned within the air (or other gas) lumen at a proximal end of the air lumen. The temperature sensor 107 is positioned within lumen 104 along with transmission wire(s) 108 in the same manner as temperature sensor 82 and wire 83 are positioned in catheter 60 described above. The system is charged by inflation of the balloon 106, i.e., preferably partially inflated for the reasons discussed above, by insertion of air via a syringe or other injection method through the side port 103 which is in fluid communication with lumen 104. The catheter 100 is a closed system with the balloon 106 sealed so that air inserted through lumen 104 and into balloon 106 cannot escape through balloon 106. Thus, a closed chamber is formed comprising the internal space of the balloon 106 and the internal lumen 104 communicating with the internal space of balloon 106. With the balloon 106 inflated, pressure monitoring can commence. When external pressure is applied to an outer surface of the balloon 106, caused by outward uterine contraction pressure which applies pressure to the bladder wall and thus against the wall of balloon 16, the air within the chamber of the balloon 106 is compressed. This compresses the air within the lumen 104 creating an air charged column along the lumen 104. The sensor 102 at the proximal end of catheter 100 measures pressure of the air column and its proximal end and can provide continuous pressure readings, converted to an electrical signal by the transducer at the proximal end or external of the catheter 100, and then electrically communicates through wire(s) 103 to an external monitor. The balloon 106, like balloon 16, balloon 66 and the other pressure balloons described herein, is of sufficiently large size to provide a sufficient circumferential area for detection of pressure changes along several parts of the bladder wall, thereby providing an average pressure and enabling more accurate pressure readings. Balloon 109 is a stabilizing balloon like balloon 76 inflated through a separate lumen.

Note the wires of the sensor 102 can terminate at the proximal end in a plug in connector which can be connected directly to the monitor or alternatively plugged into a converter to convert the signals from the transducer in the embodiments wherein the converter is interposed between the wires and monitor (see e.g. the system of FIG. 2) to provide the aforedescribed graphic display. Although, the system is capable of continuous pressure and temperature monitoring, it can also be adapted if desired for periodic monitoring so the pressure and/or temperature readings can be taken at intervals or on demand by the clinician. In all other respects, catheter 100 is identical to catheter 60 and therefore for brevity further discussion is not provided since the structure and function of the balloons, the continuous pressure monitoring, etc., as well as the aforedescribed alternative arrangements of catheter 60, are fully applicable to the catheter 100.

Figure 13A:
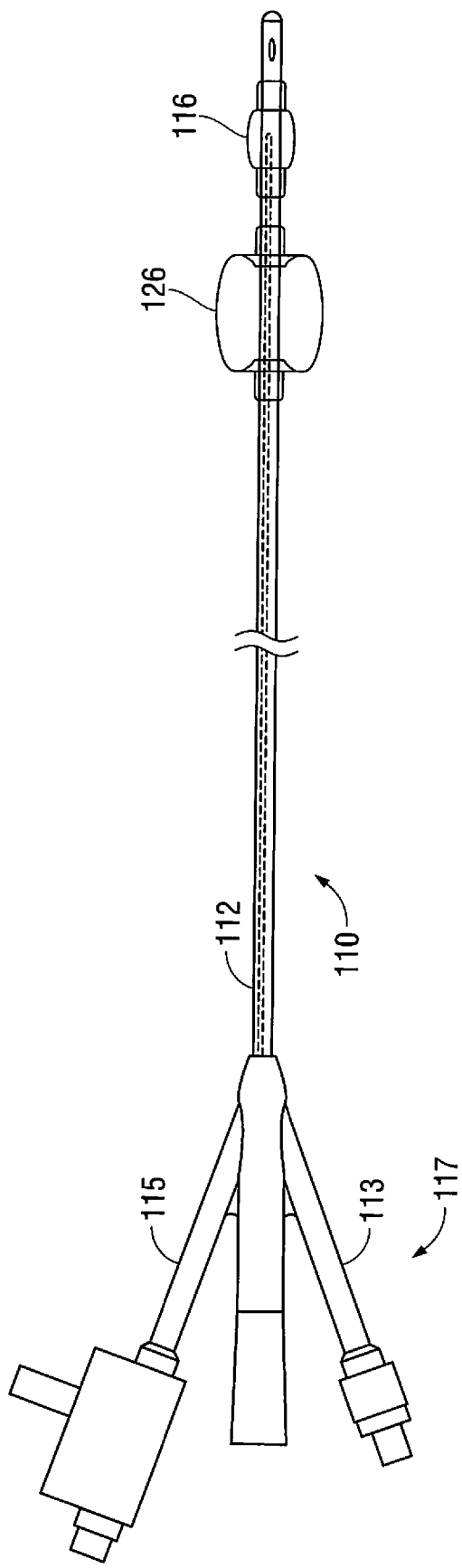
FIG. 13A is a side view of another alternate embodiment of the catheter of the present invention having two balloons and a pressure sensor positioned within the pressure balloon, the two balloons shown in the inflated condition.
Figure 13B:
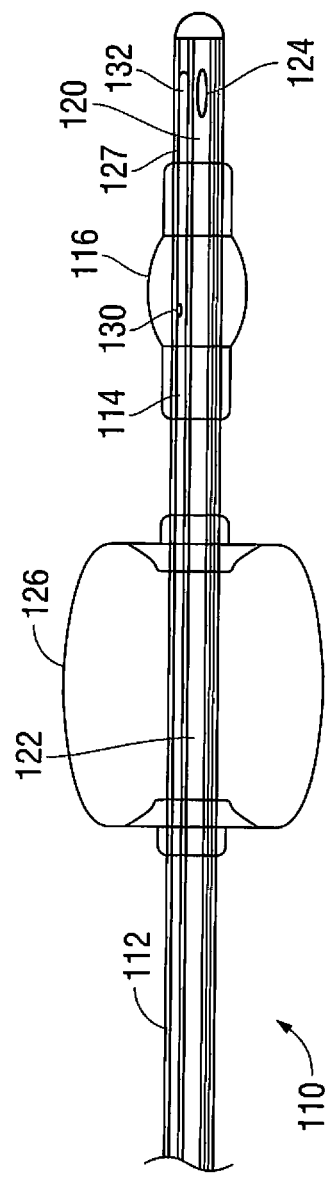
FIG. 13B is an enlarged view of the distal portion of the catheter of FIG. 13A.

FIGS. 13A and 13B illustrate an alternate embodiment wherein catheter 110 includes a pressure sensor within the balloon. More specifically, catheter 110 has an elongated flexible shaft 112 having a lumen (channel) 114 extending within the shaft 112 and communicating at its distal region with balloon 116 to fluidly communicate with balloon 116 to inflate the balloon. Balloon 116 (also referred to as the pressure balloon) is utilized for monitoring pressure. A fluid side port 115 is positioned at a proximal region 117 of the catheter 110 for communication with an infusion source for infusion of gas through the lumen 114 and into the balloon 116. The shaft 112 also includes a second lumen (channel) 120 and third lumen (channel) 122 extending therein. Second lumen 122 has a side opening 124 at a distal portion communicating with the bladder for drainage. The third lumen 122 communicates at a distal region with stabilizing balloon 126 to fluidly communicate with balloon 126 to inflate the balloon to limit movement of the catheter 110 to keep it in place within the bladder. A fluid port 113 is positioned at a proximal region 117 of the catheter 110 for communication with an infusion source for infusion of fluid through the lumen 122 and into the balloon 126.

The pressure sensor 130 is carried by catheter 110 and positioned within the balloon 116 to measure pressure in response to deformation of the balloon 116 in response to pressure exerted on an outer wall of balloon 116 due to uterine contraction pressure. The pressure transducer can include the sensor 130 or can be a separate component positioned at a proximal end of the catheter external of the catheter 110. The temperature sensor 132 can be positioned within the balloon 116, part of sensor 130, or alternatively positioned within lumen 114 (as shown in FIG. 13B), with its transmission wire(s) 127 extending within the gas, e.g., air, lumen 114 along with the wires of sensor 130 in the same manner as in catheter 60 described above.

In all other respects, catheter 110 is identical to catheter 60 and therefore for brevity further discussion is not provided since the structure and function of the balloons, lumens, continuous pressure monitoring, etc. as well as the aforedescribed alternative arrangements of catheter 60, are fully applicable to the catheter 110.

As discussed above, the pressure balloon has a large circumferential area (and large volume) to provide multiple reference points for pressure readings and to provide an average pressure to enable more accurate readings. Thus, the pressure balloon provides for gross measurement. In an alternate embodiment shown in FIG. 15, the pressure balloon for detecting pressure, designated by reference numeral 142, forms an outer balloon of catheter 140. Contained within the outer balloon 142 is an inner balloon 143. The inner balloon 143 provides a smaller diameter balloon and a smaller circumference (and volume) than the outer balloon 142. The inner balloon 143 together with the lumen 144 forms a smaller air (or other gas) column than in the embodiments discussed above where the larger balloon internal space communicates directly with the air lumen. This provides finer measurements. Thus, the compliant outer balloon 142 compresses the compliant inner balloon 143 which compresses the air within air lumen 144. The closed system is thereby formed by the internal space of the inner balloon 143 and the lumen 144. In certain instances, the smaller balloon air column can provide a more accurate reading from the average pressure determined by the larger outer balloon 142.

The inner balloon 143 and outer balloon 142 can be separately/independently inflated and closed with respect to each other so there is no communication, e.g. passage of gas or liquid, between the inner and outer balloons 143, 142.

The proximal and distal end of the inner balloon 143 in the illustrated embodiment are within the confines of the outer balloon 142, i.e., the proximal end of the inner balloon 143 is distal of the proximal end of the outer balloon 142 and the distal end of the inner balloon 143 is proximal of the distal end of the outer balloon 142. Thus the inner balloon 143 is fully encapsulated within the outer balloon 142.

With this inner/outer balloon arrangement, the larger outer surface of the outer balloon 143 takes gross measurements and then the forces are concentrated on the smaller inner balloon to amplify/concentrate pressure on the small area of the inner balloon so small changes can be detected and waves transmitted to the pressure transducer (via the length of the lumen) to a proximal transducer, e.g. an external pressure.

The pressure transducer and pressure sensor 150 can be positioned within the lumen 144 in the same manner as sensor 30 of FIG. 1 and can function in the same manner. Alternatively, the pressure transducer can be at a proximal end of the catheter 140 as in the embodiment of FIG. 12 or external of the catheter. A temperature sensor can be part of sensor 150 as in the embodiment of FIG. 1 or alternatively a separate component which can be positioned for example distal of the pressure sensor within the air lumen as in the embodiment of FIG. 8. The transmission wires of the pressure sensor 150 and the temperature sensor extend through lumen 144.

The catheter 140 can optionally include a stabilizing (retention) balloon 145 similar to balloon 76 of FIG. 8. The catheter 140 would have a lumen, e.g., lumen 146, to inflate the stabilizing balloon 145. Lumen 148 with side opening 149 provides for drainage of the bladder. Lumen 144 which is used to inflate the inner balloon 143 and create the gas column has an opening at a distal region to communicate with inner balloon 143. A separate lumen 147 has an opening at a distal region to communicate with the outer balloon 142 to fill the outer balloon 142.

In use, catheter 140 is inserted into the bladder and stabilizing balloon 145 is inflated to secure the catheter 140 in place. The system is charged by inflation of the inner balloon 143, preferably partially inflated for the reasons discussed above, by insertion of air through a side port which is in fluid communication with lumen 144 in a closed system formed by the internal space 143a of the inner balloon 143 and the internal lumen 144 communicating with the internal space 143a of inner balloon 143. Outer balloon 142 is filled, preferably partially inflated for the reasons discussed above, via injection of air through a separate lumen. With the outer balloon 142 inflated, pressure monitoring can commence as external pressure applied to the larger circumferential outer surface of the outer balloon 142 compresses and deforms the outer balloon 142 which compresses the inner balloon 143. As the inner balloon 143 is compressed and deformed in response to compression/deformation of the outer balloon 142 based on changes to bladder pressure, the sensor 150 at the distal end of lumen 144 provides continuous pressure readings, converted to an electrical signal by the transducer within the distal end of lumen 144, and then electrically communicates through wires 152 extending through lumen 144 to an external monitor either directly or via a converter. Although, the system is capable of continuous pressure and continuous temperature monitoring as in the other embodiments disclosed herein, it can also be adapted if desired for periodic monitoring so the pressure and/or temperature readings can be taken at intervals or on demand by the clinician.

Note that although separate lumens are provided for the inflation of inner balloon 143 and outer balloon 142, in an alternate embodiment, a single lumen can be utilized to inflate both balloons 143 and 142.

FIG. 16 illustrates an alternate embodiment of catheter 140, designated by reference numeral 140'. Catheter 140' is identical to catheter 140 except a larger outer balloon 142' is provided to cover more surface area for pressure readings. In all other respects, catheter 140' is identical to catheter 140 and for brevity further discussion is not provided since the features and functions of catheter 140, and its alternatives such as single or two lumens for inner and outer balloon inflation, are fully applicable to catheter 140'. For ease of understanding, the components of catheter 140' which are identical to catheter 140 are given the same reference numerals as catheter 140.

Note that the larger balloon 142' can be used with the catheters of any of the embodiments described herein. Thus, a pressure balloon of the larger size balloon 142' can be used instead of the smaller pressure balloons illustrated in the drawings. Note the size of the balloons is provided by way of example and are not necessarily drawn to scale comparatively to the other components.

FIG. 17 illustrates an alternate embodiment of catheter 140, designated by reference numeral 140". Catheter 140" is identical to catheter 140 except a pear shaped larger outer balloon 142" is provided. The larger balloon covers more surface area for pressure readings. The pear shape could in certain applications decrease the risk of obstruction and provide more tactile continuity of the balloon to the bladder wall giving a better transmission of uterine contraction pressure to the internal sensor. In all other respects, catheter 140" is identical to catheter 140 and for brevity further discussion is not provided since the features and functions of catheter 140, and its alternatives such as single or two lumens for inner and outer balloon inflation, are fully applicable to catheter 140". For ease of understanding, the components of catheter 140" which are identical to catheter 140 are given the same reference numerals as catheter 140.

Figure 17A:
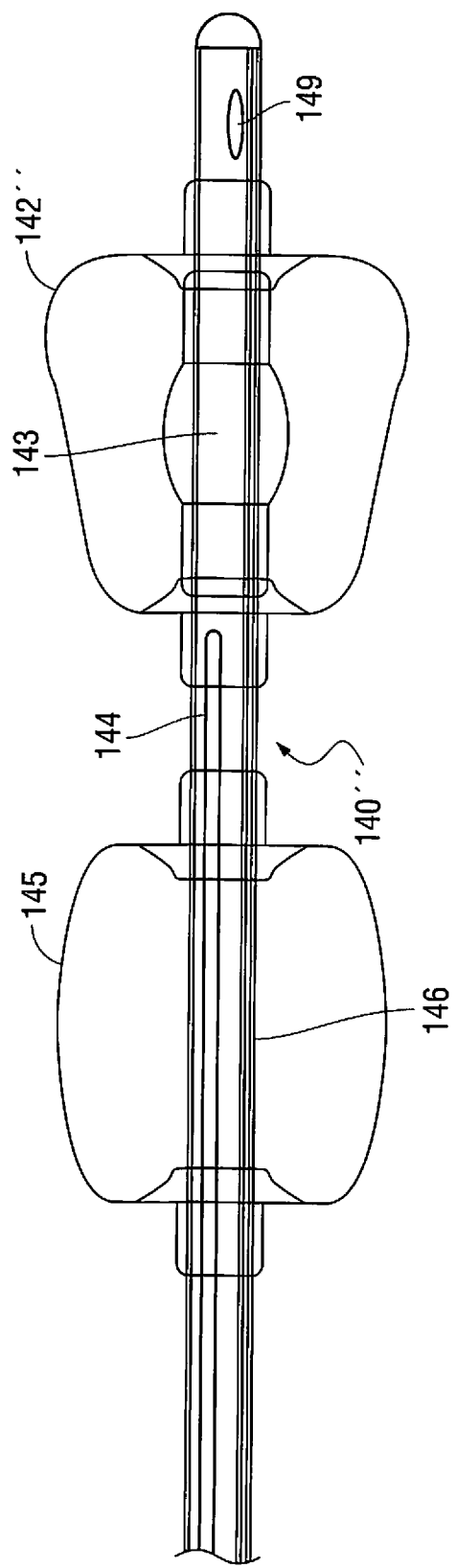
FIG. 17A is a side view similar to FIG. 15 illustrating an alternate embodiment having a pear-shaped outer balloon.
Figure 17B:
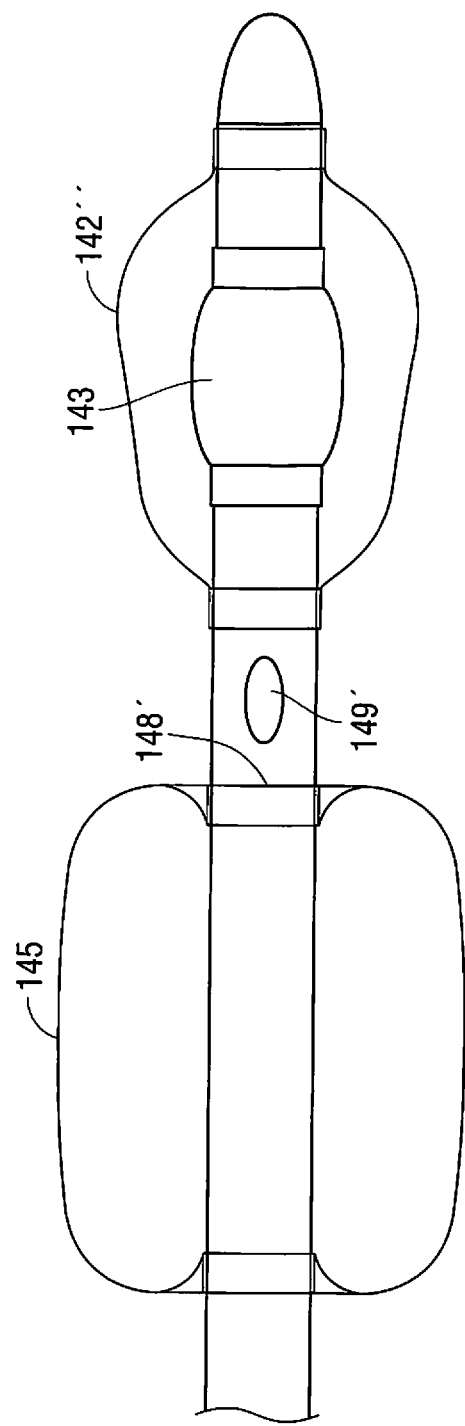
FIG. 17B is a side view similar to FIG. 17A showing an alternate embodiment wherein the drainage opening is between the stabilizing and pressure balloons.
Figure 19:
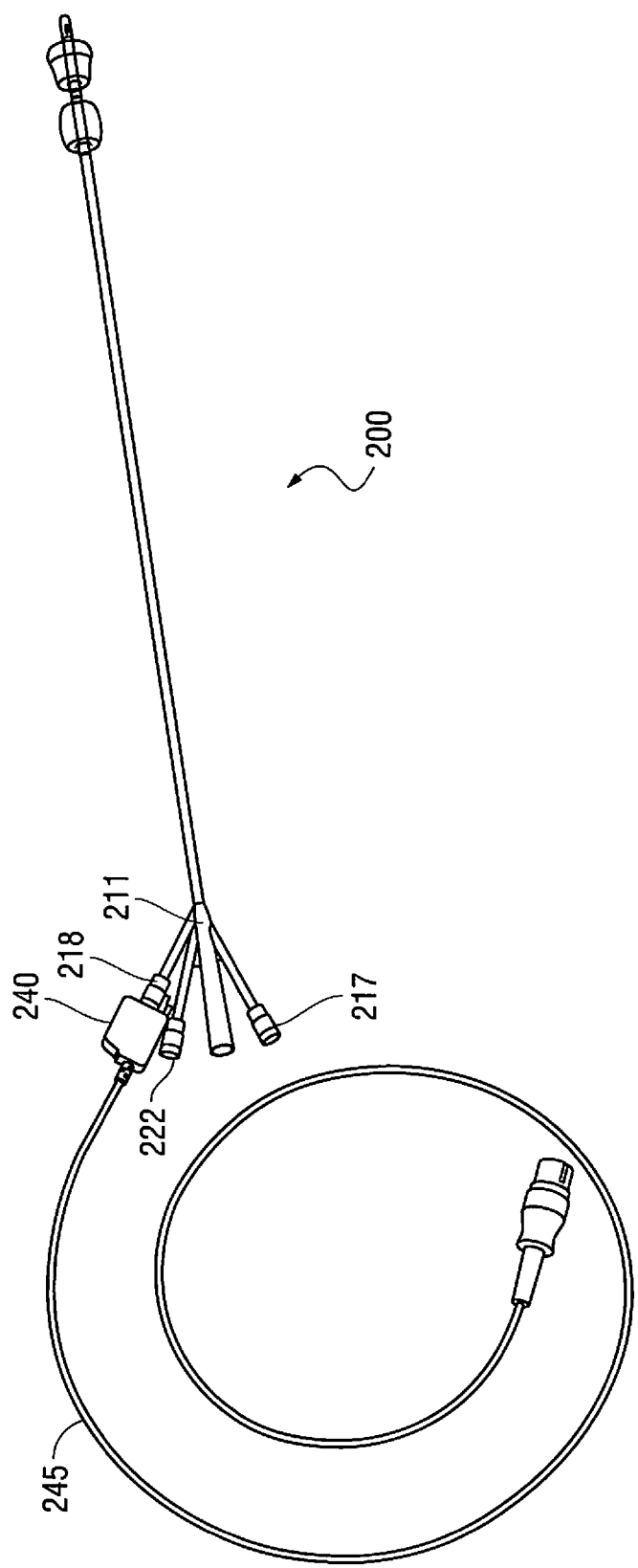
FIG. 19 is a perspective view of the catheter of FIG. 18A with a pressure transducer hub attached to the catheter.

FIG. 17B illustrates a catheter identical to catheter 140" with identical balloons, the only difference being that the side opening 149' is positioned proximal of the balloon 143 rather than distal of the balloon as in FIG. 17A. That is, opening 149', in communication with the catheter lumen 148' for drainage of the bladder, is positioned between the stabilizing balloon 145 and the inner and outer pressure (and inner) pressure balloon 142" (and 143). Thus, it is distal of the stabilizing balloon 145 and proximal of the outer balloon 142".

Note that the positioning of the side opening for drainage of FIG. 17B, which communicates with the drainage lumen of the catheter, can be utilized with any of the catheters disclosed herein. Thus, in the catheters disclosed in the various embodiments herein, instead of the drainage opening positioned distal of the pressure balloon(s), it can be proximal of the pressure balloon and distal of the stabilizing balloon so it is between the two balloons.

Note that the pear shaped balloon 142" can be used with the catheters of any of the embodiments described herein. Thus, a pressure balloon of the pear shape of balloon 142", and of larger size if desirable, can be used instead of the pressure balloons illustrated in the drawings.

FIGS. 18-25B illustrate an alternate embodiment of the catheter of the present invention. The pressure balloon for detecting pressure, designated by reference numeral 202, forms an outer balloon of catheter 200. Contained within the outer balloon 202 is an inner balloon 204. The inner balloon 204 provides a smaller diameter balloon and a smaller circumference (and volume) than the outer balloon 202. The inner balloon 204 together with the lumen 214, which communicates with the inner balloon 204 for inflation thereof, forms a smaller air column as in the embodiments of FIGS. 15-17. This provides finer measurements. Thus, the compliant outer balloon 202 compresses the outer wall 205 of the compliant inner balloon 204 which compresses the air (or other gas) within air lumen 214. The closed system is thereby formed by the internal space 204a of the inner balloon 204 and the lumen 214. The smaller balloon air column can in certain instances provide a more accurate reading from the average pressure determined by the larger outer balloon 202.

The pressure transducer and pressure sensor are external to catheter 200 and mounted to port 218 at the proximal end 201 of catheter 200. More specifically, a transducer hub or housing, designated generally by reference numeral 240, contains the pressure transducer and sensor and is mounted to the angled side port 218. In the embodiment of FIG. 18A, the hub 240 is mounted over the port 218 and can be locked or secured thereto such as by a friction fit, snap fit, threaded attachment, a latch, etc., maintaining an airtight seal so the air is contained within the lumen 214 and balloon 204. The hub 240 has an elongated (rod-like) member or nose 242 extending distally therefrom (FIG. 24A) dimensioned to be inserted through the proximal opening in port 218 and into air lumen 214. (Note the air lumen 214 as the other lumens extend into their respective angled side ports). The elongated member 242 also has a channel 244 extending therethrough to allow the pressure wave to travel through to the pressure sensor. Although in preferred embodiments no additional air needs to be injected into inner balloon 204 via lumen 214 after attachment of hub 240, it is also contemplated that a port or opening can be provided in hub 240 to receive an injection device for injection of additional air. Such additional air can communicate with and flow through channel 244 of elongated member 242, into lumen 214 and into inner balloon 204 for inflation, or alternatively, a side port or opening in angled port downstream of the elongated member 242 could be provided.

To charge the system, when the hub 240 is mounted to the side port 218, the elongated member 242 extends into lumen 214 to advance air through the air lumen 214 into inner balloon 204 to expand inner balloon 204. In some embodiments, 0.2 cc of air can be displaced/advanced by the member 242, although other volumes are also contemplated. Thus, as can be appreciated, mounting of the hub 240 to the catheter 200 automatically pressurizes the air lumen/chamber and expands the inner balloon 204. Note the inner balloon 204 can be partially or fully inflated (expanded), dependent on the amount of air advanced into the inner balloon 204. Further note that the lumen 214 is not vented to atmosphere when the transducer hub 240 is attached and air is advanced through the air lumen. The port 218 can include a closable seal through which the elongated member 242 is inserted but maintains the seal when the elongated member 242 remains in the lumen 214.

Lumen 214 which is used to inflate the inner balloon 204 and create the air column has an opening at a distal region to communicate with the interior of inner balloon 204. Lumen 212 of catheter has an opening at a distal region to communicate with the outer balloon 202 to fill the outer balloon 202. Angled port (extension) 222 at the proximal end of catheter 200 receives an inflation device to inflate, either fully or partially, the outer balloon 202.

Note as in the other embodiments disclosed herein, air is described as the preferred gas for creating the column and expanding the balloon, however, other gasses are also contemplated for each of the embodiments herein.

Figure 20A:
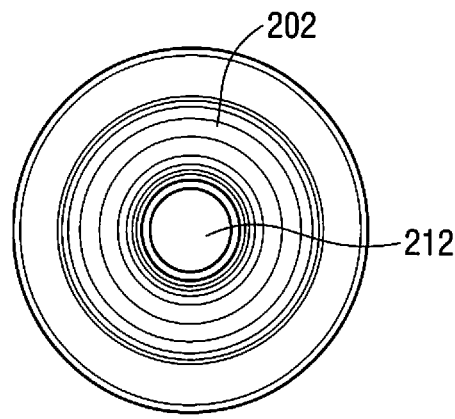
FIGS. 20A, 20B and 20C are enlarged front, side and perspective views of the outer balloon of FIG. 18A in the expanded condition.
Figure 20B:
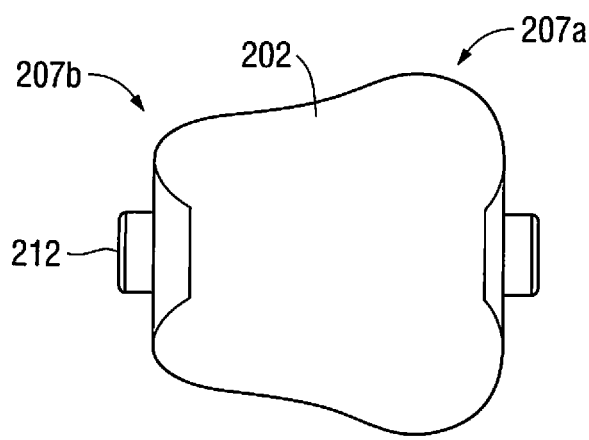
Figure 20C:
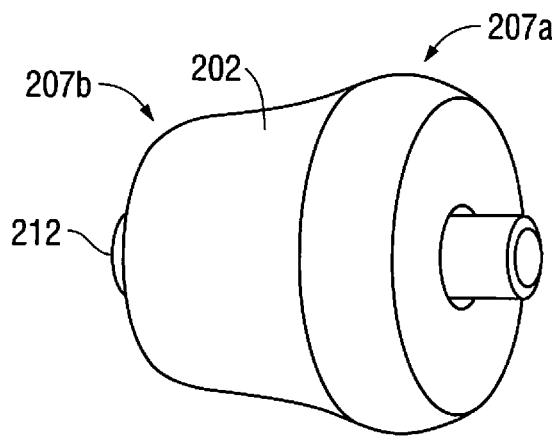
Figure 21A:
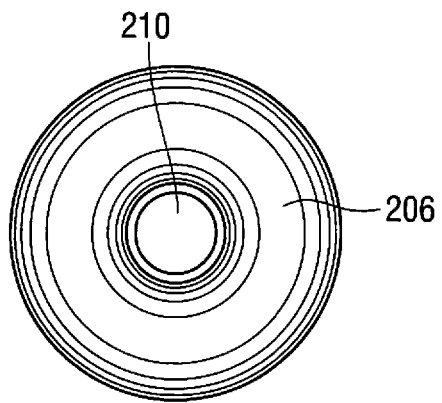
FIGS. 21A, 21B and 21C are enlarged front, side and perspective views of the stabilizing balloon of FIG. 18A in the expanded condition.
Figure 21B:
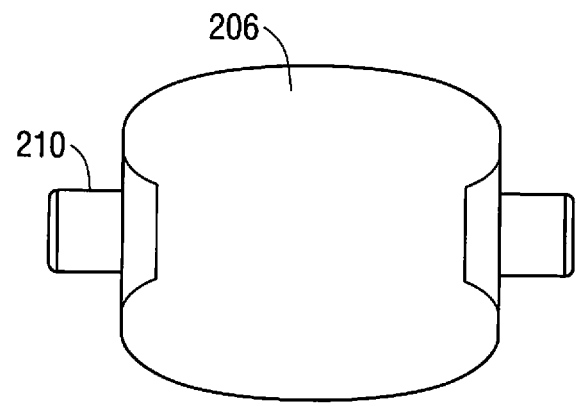
Figure 21C:
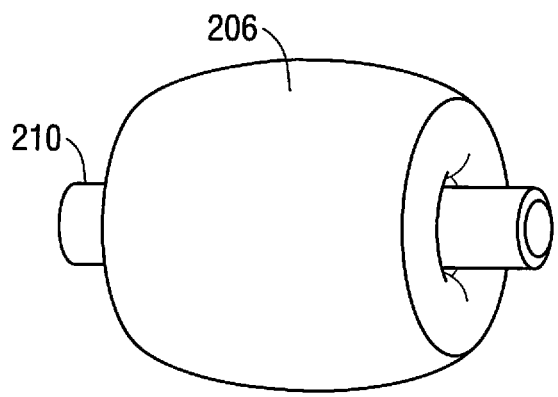
Figure 22A:
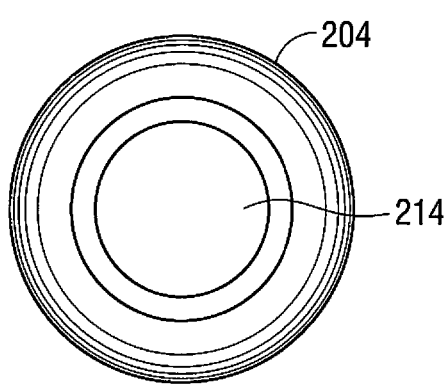
FIGS. 22A, 22B and 22C are enlarged front, side and perspective views of the inner balloon of FIG. 18A in the expanded condition.
Figure 22B:
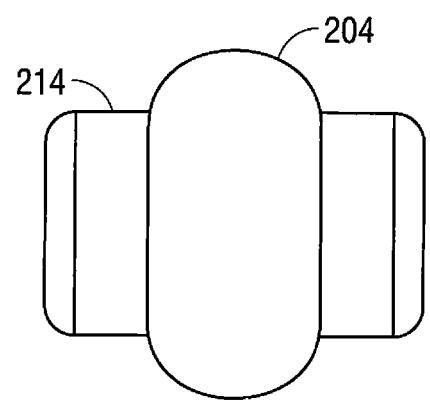
Figure 22C:
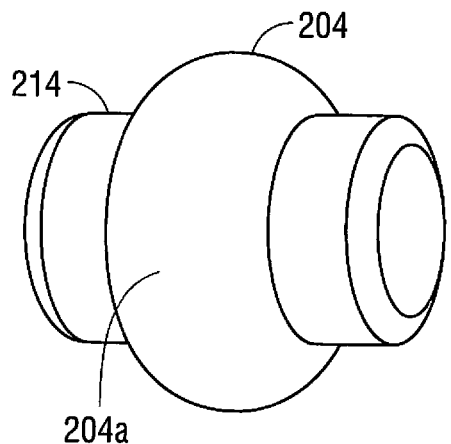

The outer balloon 202 can be shaped such that a distal region 207a (FIGS. 20A-20C) has an outer transverse cross-sectional dimension, e.g., diameter, greater than an outer transverse cross-sectional dimension, e.g., diameter, of the proximal region 207b. A smooth transition (taper) can be provided between the distal region 207a and proximal region 207b. Note the balloon 202 can be pear shaped as shown in FIGS. 20B and 20C although other configurations are also contemplated. This pear shape in some applications is designed to conform to the shape of the bladder.

The inner and outer balloons 204, 202 can by way of example be made of urethane, although other materials are also contemplated.

Figure 25A:
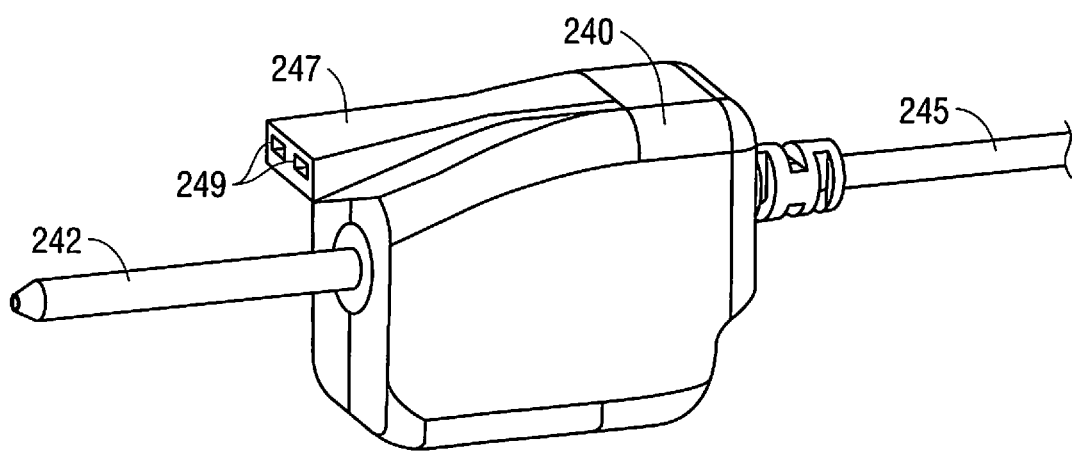
FIG. 25A is a perspective view of the transducer hub of FIG. 24A.
Figure 25B:
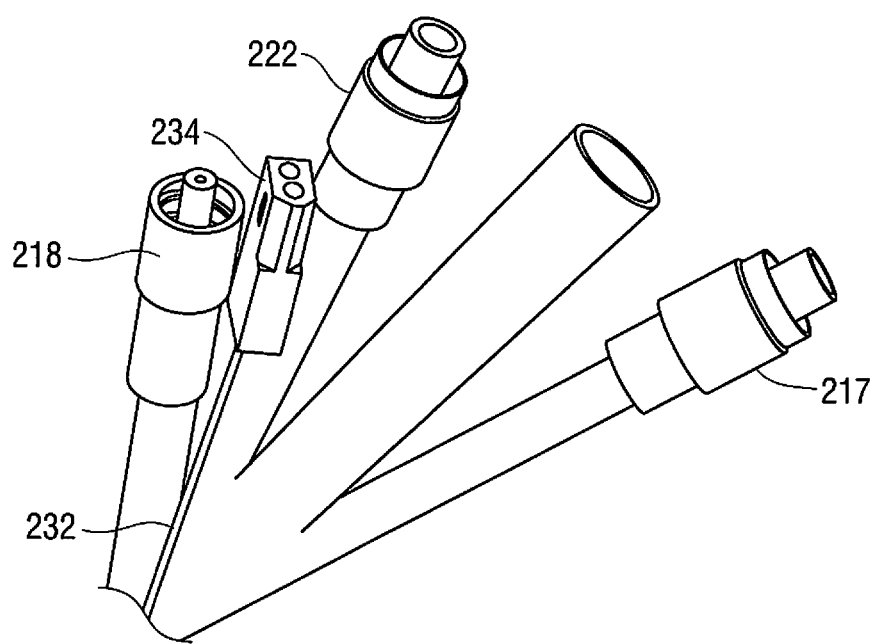
FIG. 25B is a perspective view of the proximal end of the catheter showing a connector for the thermocouple wire.

A temperature sensor 230, such as a thermocouple, is positioned within the catheter 200 at a distal end to measure maternal core body temperature. The sensor 230 is shown positioned in a lumen 216 separate from the lumens 214 and 212. One or more wires 232 extend from the sensor 230 through the lumen 216, exiting the lumen 216 and catheter 200 at a proximal end 216a between the angled extensions/ports of the catheter 200, e.g., between the port 218 for the inner balloon 204 and the port 222 for the outer balloon 202. A connector 234, e.g., a male connector, is at the proximal terminal end of the wire 232 as shown in FIG. 25B. The transducer hub 240 includes a connector 247 with openings 249 (FIG. 25A) which receive the connector 234 of the wire 232. When the hub 240 is mounted to port 218 of catheter 200, the connector 234 of the wire is automatically connected to a connector carried by or within the hub 240 which is in communication with a temperature monitor. Note the connector, e.g., female connector, within or carried by the hub 240 can already be mounted to an external temperature monitor via a cable when the hub 240 is mounted to catheter 218 or alternatively the hub 240 can first be mounted to port 218 of the catheter 200 and then a cable is connected between the temperature monitor and catheter 200. In the illustrated embodiment of FIG. 25A, the wire connector 234 can plug into the openings of connector 247 positioned on the hub 240. Note the connector 247 can also be internal of the hub with an opening in the wall of the hub to enable access for the wire connector. Also note that alternatively the wire can include a female connector and the hub can have a male connector. Other types of connectors/connections are also contemplated.

As can be appreciated, connection of the transducer hub 240 to the catheter 200 (port 218) a) automatically connects the temperature sensor 230 to a connector for communication with a temperature monitor cable; and b) automatically advances air through the first lumen 214 to expand the inner balloon 204.

The catheter 200 can optionally include a stabilizing (retention) balloon 206 similar to balloon 76 of FIG. 8A. The stabilizing balloon 206 can be made of silicone, although other materials are also contemplated. If provided, the catheter 200 would have a lumen, e.g., lumen 208, to inflate the stabilizing balloon 206. Angled side port 217 can be provided in communication with lumen 208 for injection of a liquid or gas to expand the stabilizing balloon 206. The foregoing description of the stabilizing balloons is fully applicable to balloon 206. Catheter 200 also includes a lumen 211 with a distal side opening 211a (FIG. 18B) to provide for drainage of the bladder as in the aforedescribed embodiments. In the illustrated embodiment, the side opening 211a is distal of outer balloon 202 and inner balloon 204 and distal of the stabilizing balloon 210 which as shown is proximal of outer balloon 202 and inner balloon 204. In alternate embodiments, the stabilizing balloon 206 can be distal of the outer balloon 202.

Figure 23:
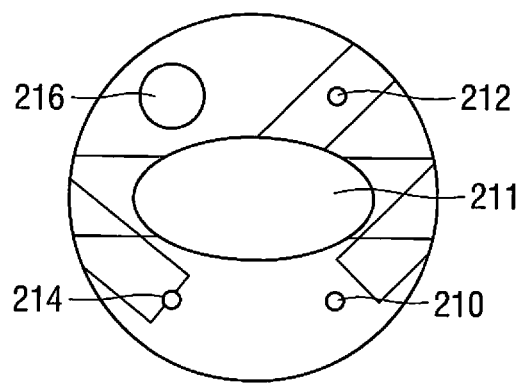
FIG. 23 is a transverse cross-sectional view of the catheter of FIG. 18A illustrating the five lumens of the catheter.
Figure 24A:
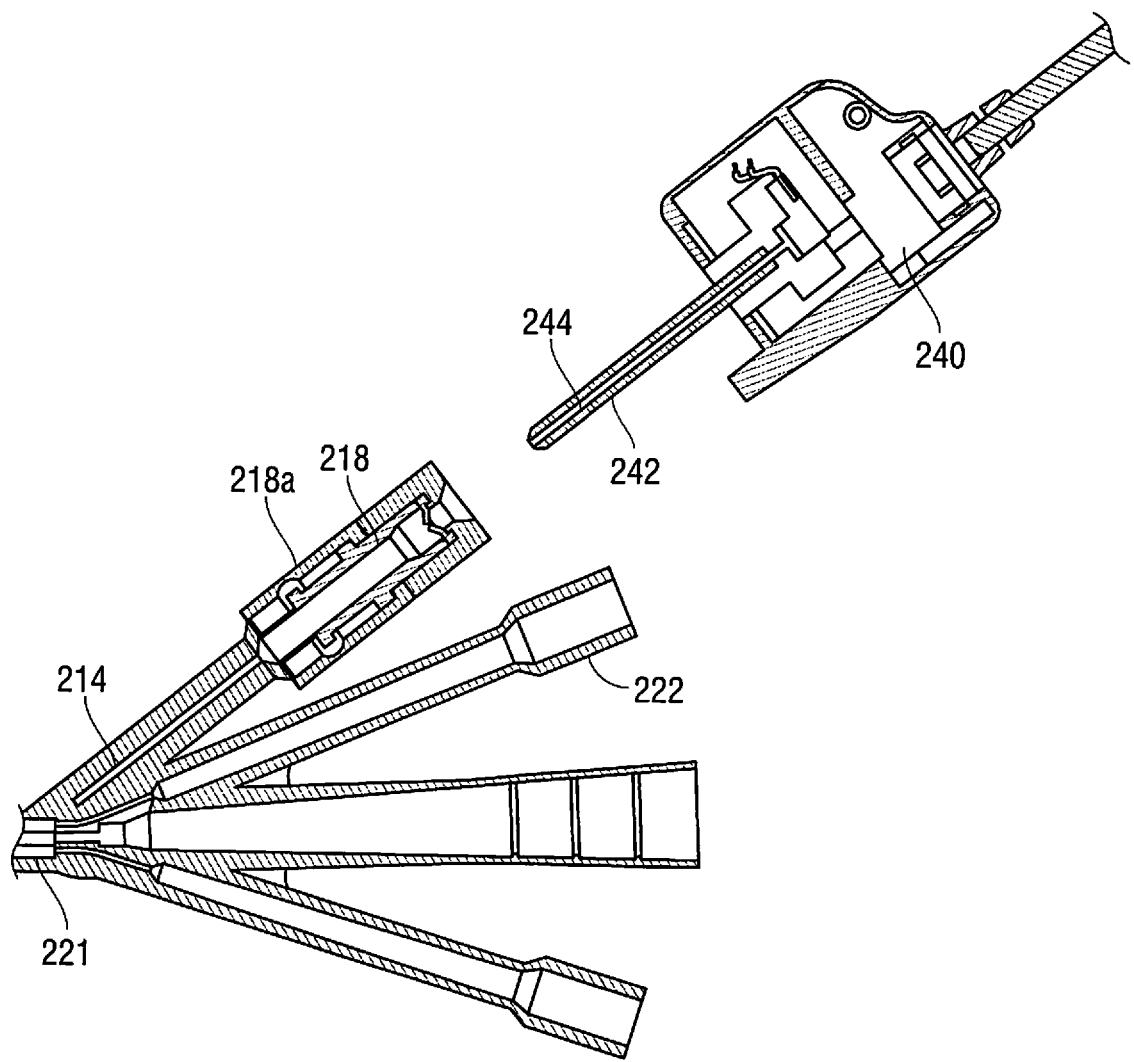
FIG. 24A is a cutaway side view showing the pressure transducer hub prior to connection to the catheter of FIG. 18A, a portion of the hub wall and catheter connector removed to show internal components.
Figure 24B:
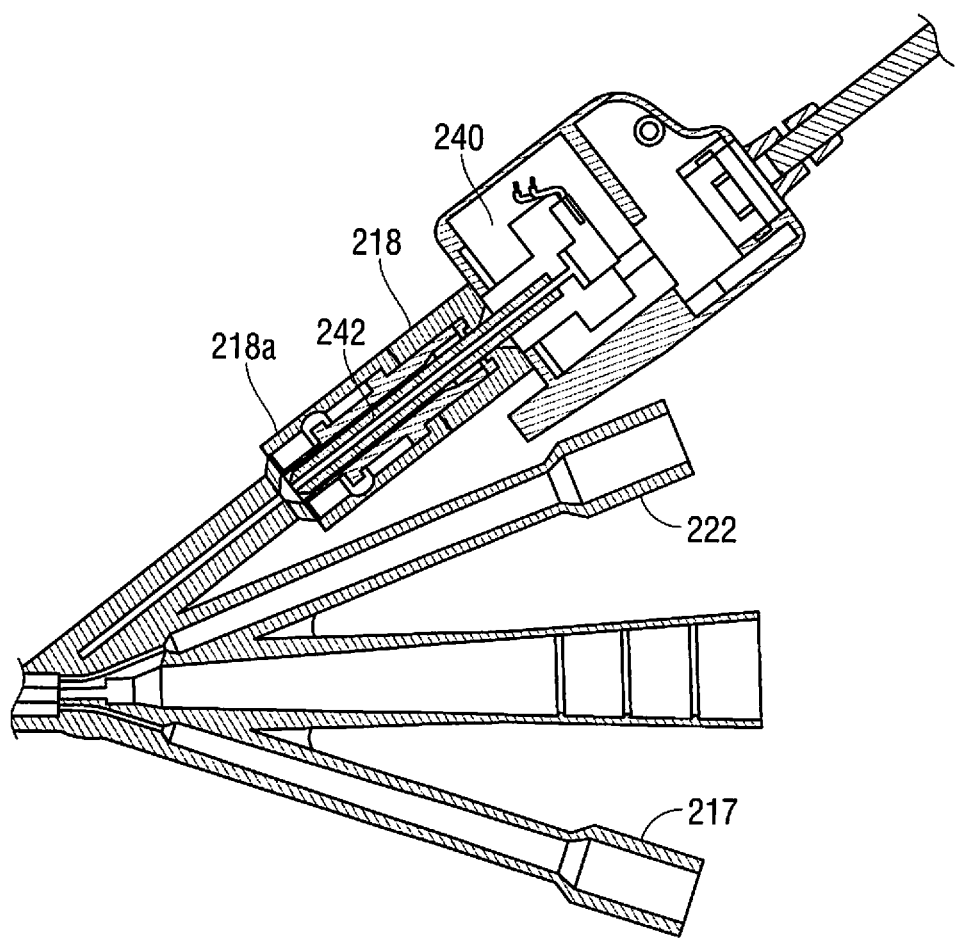
FIG. 24B is a side view similar to FIG. 24A showing the hub attached to the catheter.

Thus, in the embodiment of FIG. 18A, catheter 200 has five lumens: 1) lumen 214 communicating with inner balloon 204 to inflate the inner balloon 204 and forming the air filled chamber; 2) lumen 212 communicating with outer balloon 202 for inflating outer balloon 202; 3) lumen 210 communicating with the stabilizing balloon 206 to inflate stabilizing balloon 206; 4) drainage lumen 211 having a side opening 211a at a distal end for drainage of the bladder; and 5) lumen 216 for the temperature sensor and sensor wire(s) 232. Catheter 200 also has three angled extensions/ports at its proximal end 201: 1) port 218 for access to lumen 214 to inflate the inner balloon 204; 2) port 222 for access to lumen 212 to inflate outer balloon 202; and 3) port 217 for access to lumen 210 to inflate stabilizing balloon 206. Drainage lumen 211 extends linearly terminating in opening 223. Lumen 216 terminates proximally at the region of the angled ports 218, 222 through which wire 232 can exit from the catheter 200 for connection to a temperature monitor via hub 240. Note the location of the ports can vary from that illustrated in FIG. 18. Also, the cross-sectional dimension and size of the lumens can vary from that shown in FIG. 23 as FIG. 23 provides just one example of the size, e.g., diameter, of the lumen as well as one example of the shape/cross-sectional configuration and location. The catheter 200, as in the foregoing embodiments, can have an atraumatic tip 209.

In use, catheter 200 is inserted into the bladder and stabilizing balloon 206 is inflated to secure the catheter 200 in place. The system is charged by inflation of the inner balloon 204, preferably partially inflated for the reasons discussed above, by advancement of air through lumen 214 upon attachment of the pressure transducer 240 to the port 218 of catheter 200. Such attachment moves elongated member 242 into lumen 214 to displace the air (or other gas) already in the lumen 214 to expand the inner balloon 204. A closed system is formed by the internal space 204a of the inner balloon 204 and the internal lumen 214 communicating with the internal space 204a of inner balloon 204. In a preferred embodiment, additional air does not need to be added to the balloon 204/lumen 214. Outer balloon 202 is filled, preferably partially inflated for the reasons discussed above, via injection of air through the separate port 219 which communicates with lumen 212 of catheter 200. With the outer balloon 202 inflated, pressure monitoring can commence as external pressure applied to the larger circumferential outer surface of the outer balloon 202 compresses and deforms the outer balloon 202 which exerts a force on outer wall 205 of inner balloon 204 and compresses the inner balloon 204. As the inner balloon 204 is compressed and deformed in response to compression/deformation of the outer balloon 202 based on changes to bladder pressure (as a result of uterine contraction pressure), the pressure sensor within the external hub 240 attached at the proximal end of the catheter 200 provides continuous pressure readings, converted to an electrical signal by the transducer within the hub 240, and then electrically communicates through a connector, e.g. cable 245, to an external monitor either directly or via a converter to display pressure readings. Although, the system is capable of continuous pressure and continuous temperature monitoring, it can also be adapted if desired for periodic monitoring so the pressure and/or temperature readings can be taken at intervals or on demand by the clinician. Temperature readings are also taken during the procedure as temperature sensor 230 is connected to a temperature monitor via wire 232 connected to a connector of hub 240 which is connected to the temperature monitor, either directly or indirectly via a converter, to display temperatures. The temperature monitor can be separate from the pressure display monitor or alternatively integrated into one monitor. Cable 245 can connect to the temperature monitor as well (directly or via a converter) or a separate cable extending from the hub 240 could be provided for connection to the temperature monitor.

Note that although separate lumens are provided for the inflation of inner balloon 202 and outer balloon 204, in an alternate embodiment, a single lumen can be utilized to inflate both balloons 202 and 204. In such embodiment, catheter 200 can have one less angled port and one less lumen since inflation of the outer balloon 202 would be through port 218 and lumen 214.

As noted above, preferably no additional air needs to be added after mounting of hub 240. However, it is also contemplated that in alternate embodiments a port can be provided in communication with hub 240 to enable subsequent injection of air though lumen 214 and into inner balloon 204. Additionally, outer balloon 202 can in some embodiments receive additional fluid injection via port 222 during the procedure.

Figure 26:
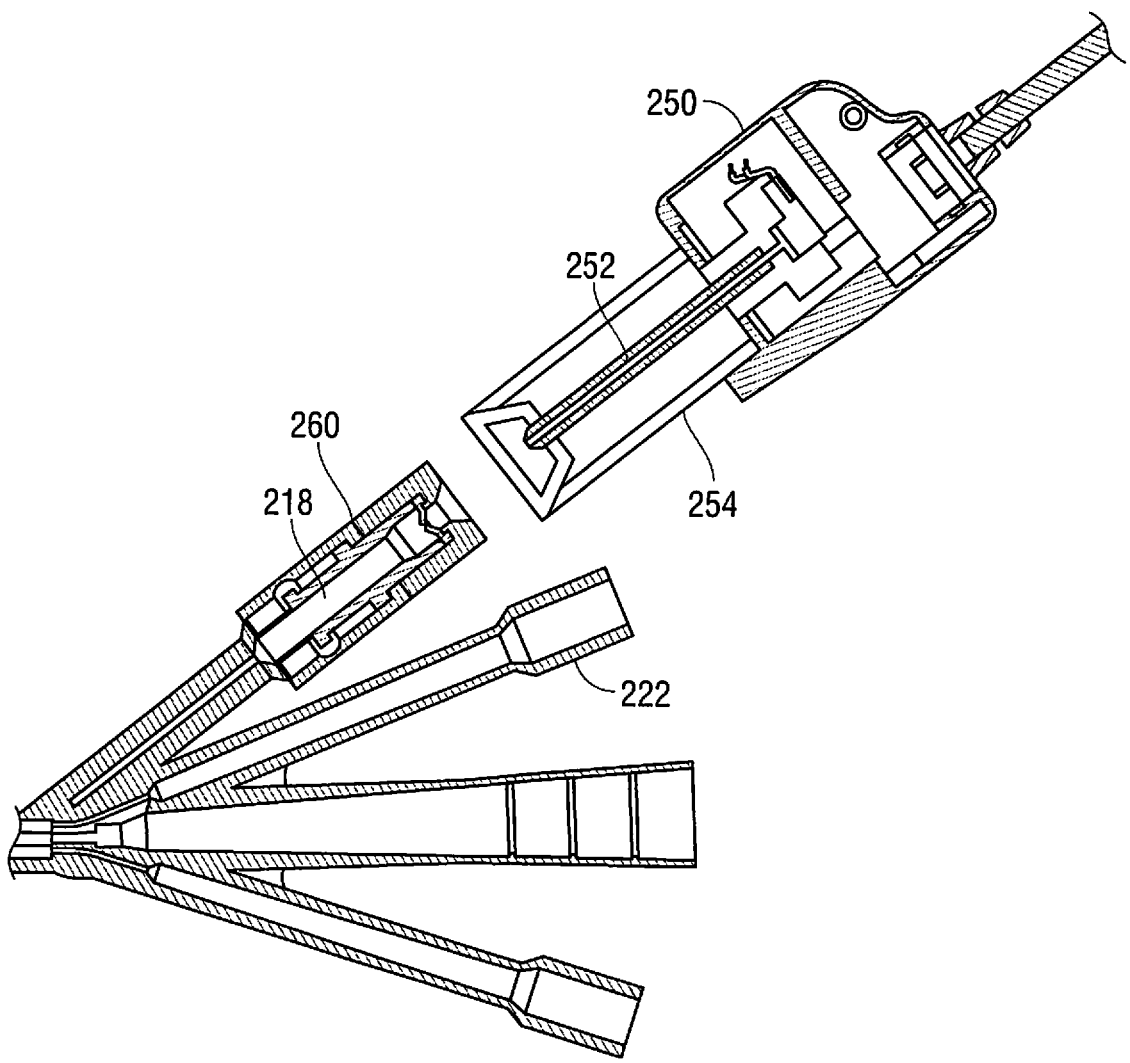
FIG. 26 is a side view of an alternate embodiment of the pressure transducer hub having a shroud over the elongated member for snap fitting onto the catheter.

FIG. 26 illustrates an alternate embodiment of the pressure transducer hub. In this embodiment, hub 250 has a shroud 254 (shown schematically) positioned over elongated member 252. This helps protect/shield the elongated member 252. When the transducer 240 is mounted to the port 260 of the catheter, the shroud 254 fits over cover 260 of port 218 and is retained by a snap fit or by other methods of securement.

Figure 27:
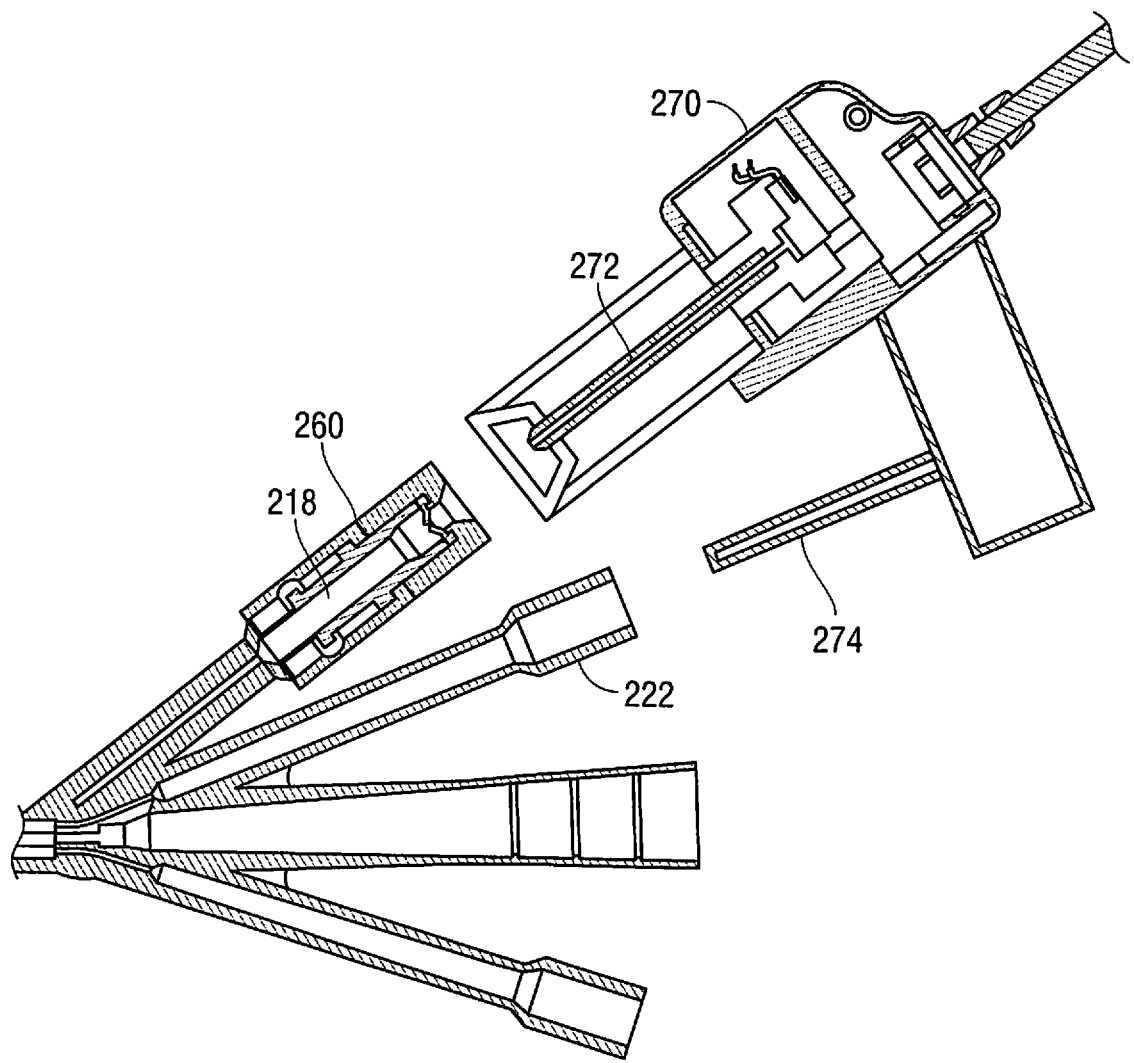
FIG. 27 is a schematic view of an alternate embodiment of the pressure transducer hub extendable into two side ports of the catheter.

In the aforedescribed embodiment, mounting of the transducer hub a) automatically connects the temperature sensor to a connector for communication with a temperature monitor cable; and b) automatically advances air through the first lumen to expand the inner balloon. In the embodiment of FIG. 27, the pressure transducer hub 270 has a second elongated member 274 extending therefrom. When transducer hub 270 is mounted to the catheter, e.g., port 218, elongated member 272 enters the air lumen in the same manner as elongated member 242 of FIG. 24B. Additionally, elongated member 274 automatically enters the lumen 210 at port 222 which communicates with the outer balloon 202. Therefore, in this embodiment, mounting of the transducer hub 270 a) automatically connects the temperature sensor to a connector for communication with temperature monitor cable as in the embodiment of FIG. 18-25B; b) automatically advances air through the first lumen to expand the inner balloon as in the embodiment of FIG. 18-25B; and c) automatically advances air through lumen 210 communicating with the outer balloon 202 to inflate (expand) the outer balloon 202. The catheter of FIG. 27 (and FIG. 26) is otherwise identical to catheter 200 of FIG. 18 so for brevity further discussion is not provided since the description of the function and elements of catheter 200 are fully applicable to the catheter of FIG. 27 (and to the catheter of FIG. 26).

FIGS. 28A-28D show an alternate embodiment of the hub/connector. The pressure transducer is external to catheter 280 and mounted to port 282 at the proximal end 281 of catheter 280 via connector (housing) 290. Catheter 280 is identical to catheter 200 of FIG. 18A except for the connector and transducer hub.

Figure 28A:
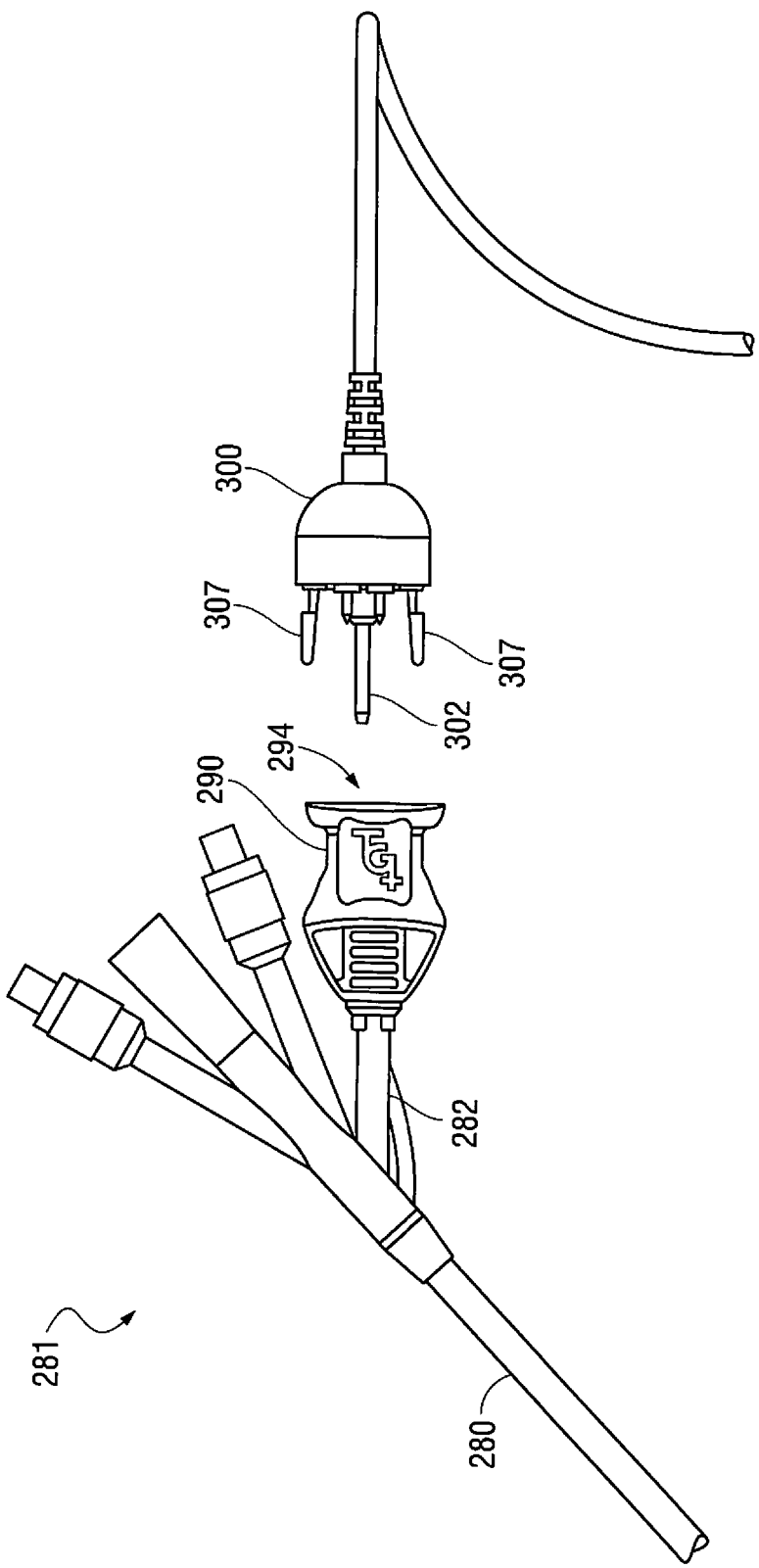
FIG. 28A is a perspective view of an alternate embodiment of the transducer hub and connector.
Figure 28B:
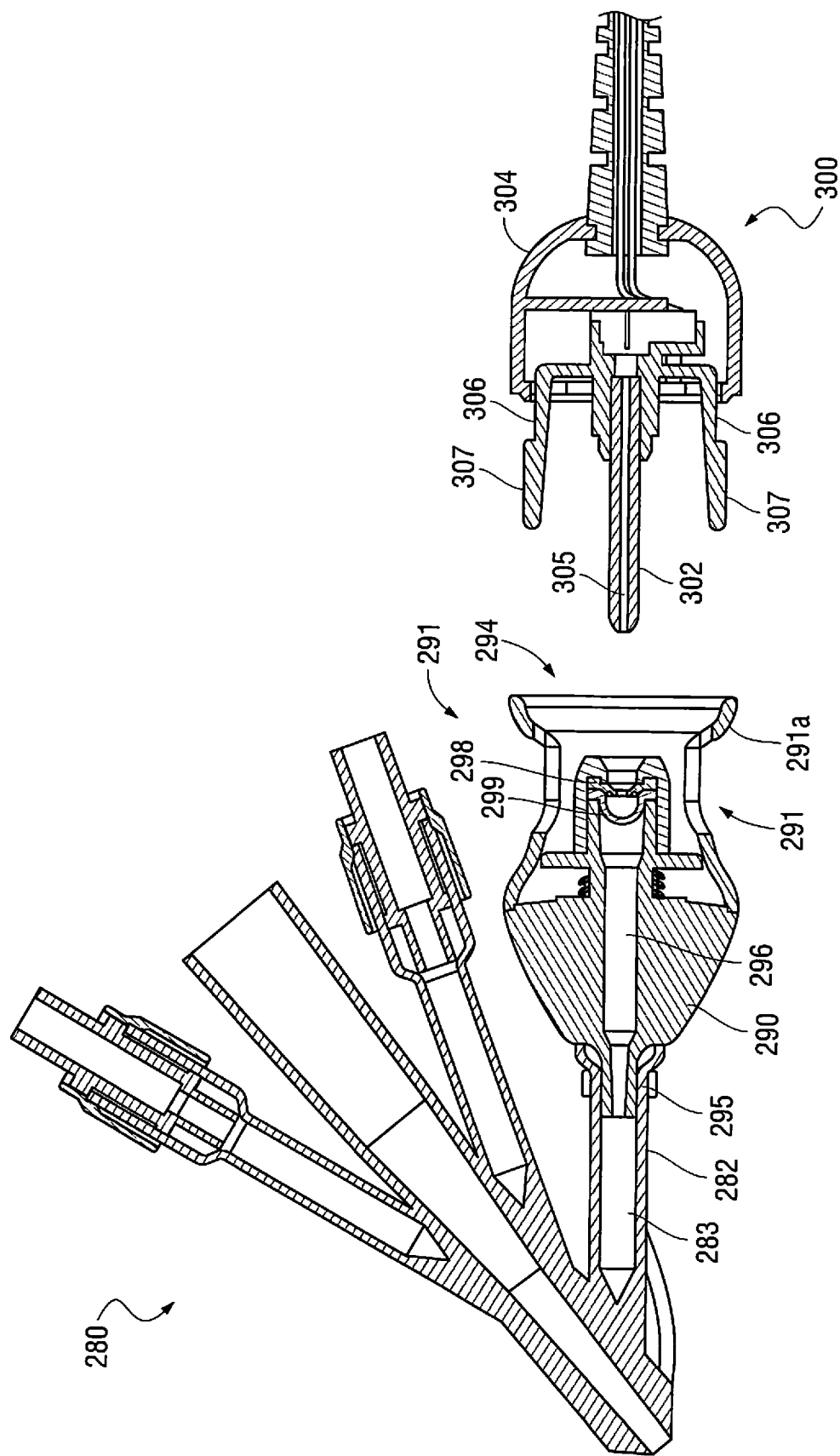
FIG. 28B is a cutaway side view of the hub and connector showing the pressure transducer prior to connection to the catheter of FIG. 18A, a portion of the hub wall and connector removed to show internal components.
Figure 28C:
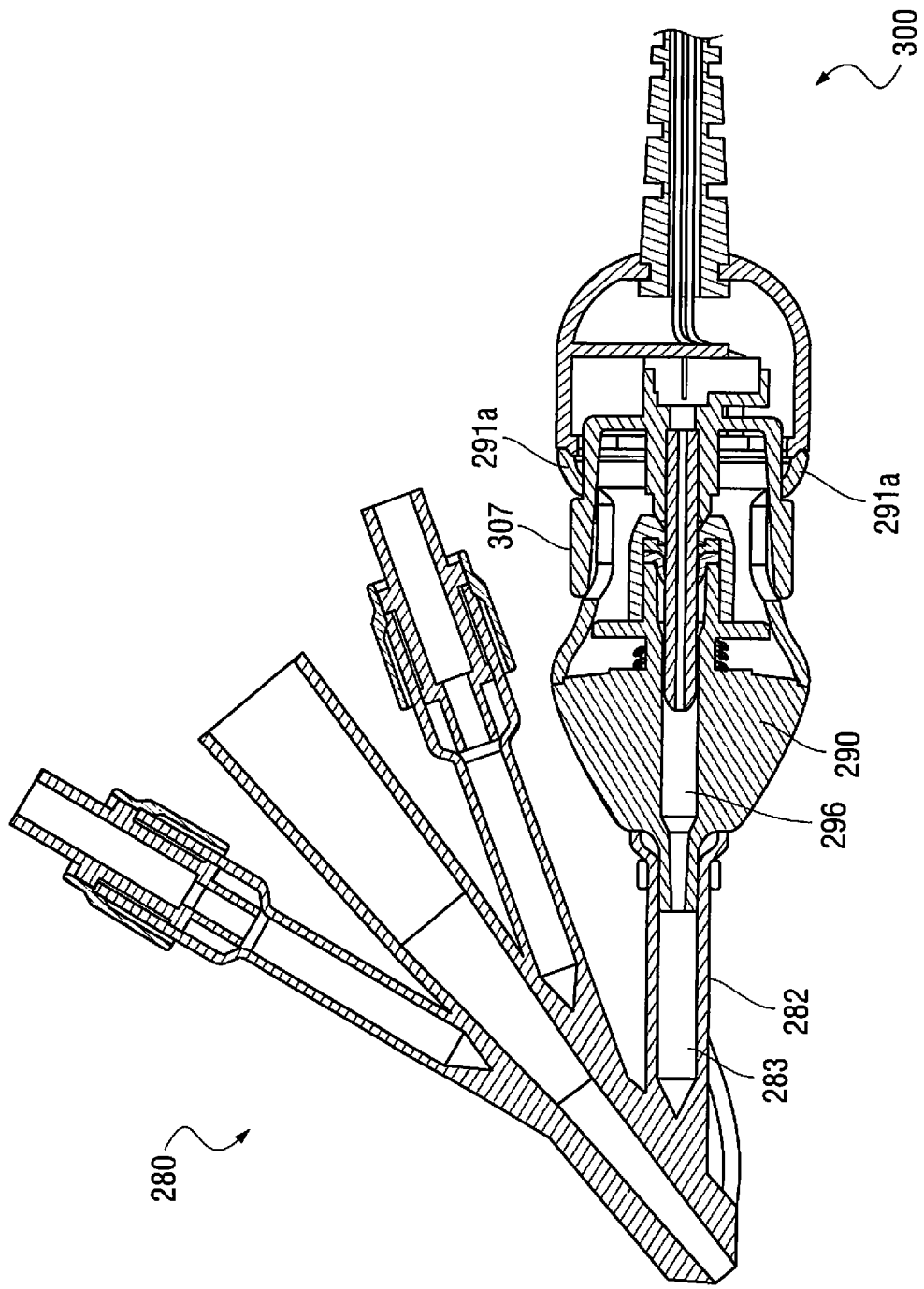
FIG. 28C is a cutaway side view similar to FIG. 28B showing the hub attached to the catheter.
Figure 28D:
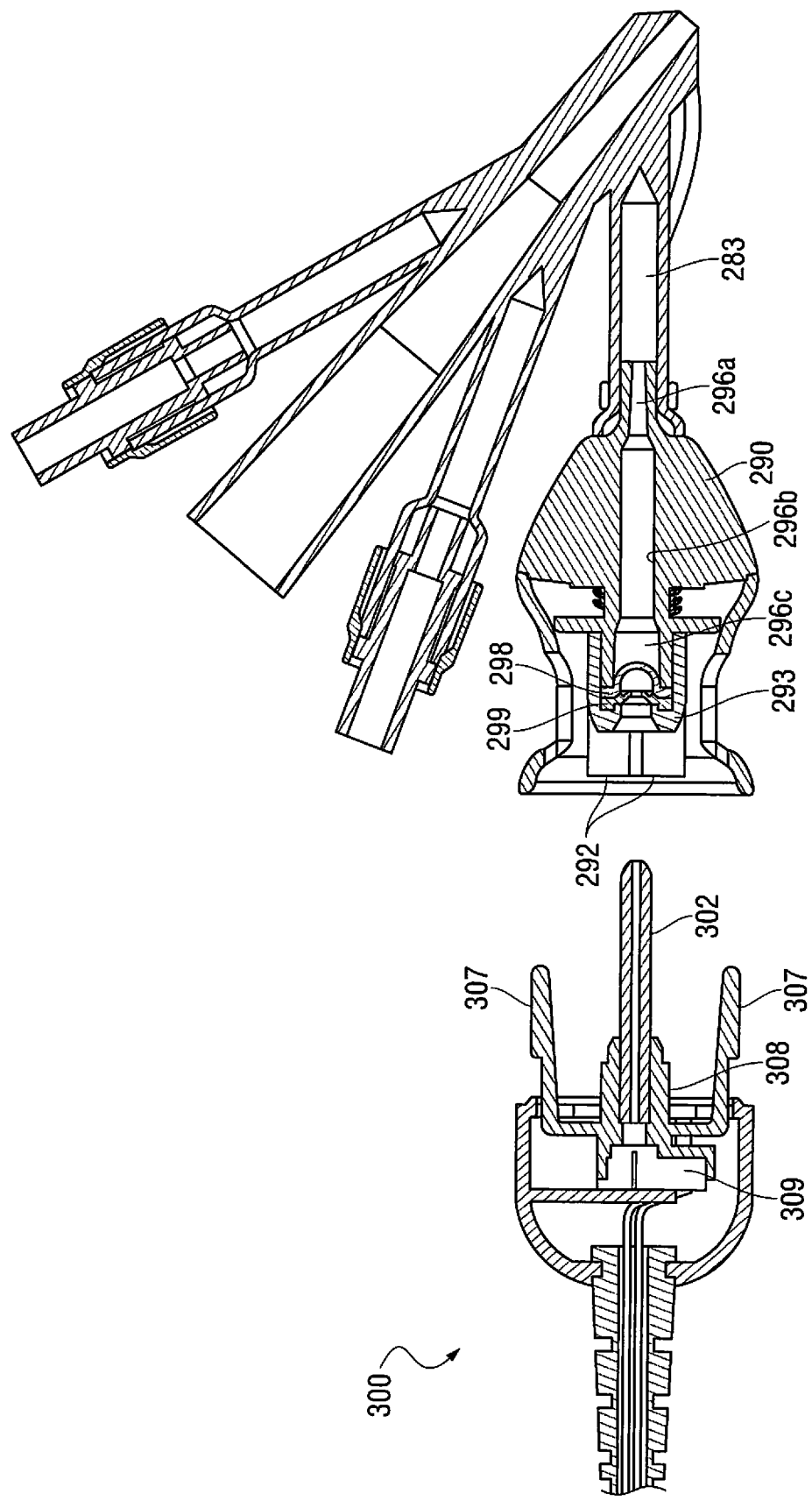
FIG. 28D is a cutaway side view similar to FIG. 28B from the other side.

More specifically, a transducer hub or housing, designated generally by reference numeral 300, contains the pressure transducer and sensor 309 and is mounted to the angled side port 282. In the embodiment of FIG. 28A, the hub 300 is mounted to the catheter 280 by connection to housing 290. Housing 290 is connected to port 282 via a barbed fitting 295 providing an interference fit with the port 282. The hub 300 is locked or secured to connector 290 such as by a snap fit provided by the latch arms discussed below, although other attachments are also contemplated such as a friction fit, threaded attachment, other form of latch, etc., as well as other types of snap fits to provide an attachment that maintains an airtight seal so the air is contained within the air lumen and balloon 92 of the catheter 280. (As noted above catheter 280 is identical to catheter 200 except for its connector so catheter 280 includes (not shown) the inner and outer pressure balloons, stabilizing balloon, temperature sensor, etc. The catheter 280 can also have a single balloon as in the aforementioned embodiments).

The housing 290 attached to catheter 280 has a proximal opening 294 and a channel (lumen) 296 to receive an elongated (rod-like) member or nose 302 extending distally from transducer hub 300. As shown channel 296 has a first diameter region 296a to match with the lumen 283 of the port 282, a second larger diameter region 296b proximal of region 296a to receive the male rod 302 of the hub 300, and a still larger diameter region 296c proximal of region 296b to receive the valve 299 and valve 298 and allow expansion thereof. As shown, valve 298 is dome shaped and is distal of valve 299. Conical cap 293, proximal of valve 299, provides a lead in to the valve 299 for the rod 302. Thermistor pins 292 receive thermistor connectors 308. Note valves 288, 299 are one example of valves that can be provided as other valves to provide an airtight seal are also contemplated.

Hub 300 is mounted to connector 290 and includes a housing 304 from which a pair of distally extending snap fit connector arms 306 extend. The arms 306 are sufficiently flexible to enable attachment and have an enlarged distal portion 307, illustratively shown as arrow shaped although other enlarged shapes could be provided. The elongated member 302 extends between the connector (latch) arms 306. When the hub 300 is mounted to the connector 290, the elongated member 302 extends into the channel 296 to advance air to inflate the inner balloon. The enlarged ends 307 of latch arms 306 enter recesses 291 of connector 290 and engage shoulders 291a to retain the hub 300. Note to release the hub 300, the ends 307 of latch arms 306 are pressed radially inwardly to disengage from shoulder 291a and the hub 300 is pulled proximally.

The housing (connector) 290 has a lumen 296 for communication with the lumen 283 in the side port 282 of catheter 280 which communicates with the air lumen and inner balloon of the catheter 280. As noted above, the lumen 296 is dimensioned to receive the elongated rod 302 of transducer hub 300. The wire for the sensor extends in housing 300. When transducer hub 300 is attached to connector 290, such attachment inserts the elongated rod 302 into lumen 296 to advance air though the air lumen in the catheter and into the balloon 204. (Note the air lumen extends into its angled side port 282). The elongated member 302 also has a channel or lumen 305 extending therethrough to allow the pressure wave to travel through to the pressure sensor. Although in preferred embodiments no additional air needs to be injected into balloon 204 after attachment of hub 300, it is also contemplated that a port or opening can be provided in hub 300 to receive an injection device for injection of additional air. Such additional air can communicate with and flow through channel 305 of elongated member 302, into the air lumen and balloon 204 for inflation, or alternatively, a side port or opening in the angled port downstream of the elongated member 302 could be provided. Attachment of hub 300 to housing 290 also automatically connects thermistor connectors 308 to thermistor pins 292 to automatically connect the temperature sensor to the hub 300 for communication via a cable to a temperature monitor.

To charge the system, when the hub 300 is mounted to the side port 282 via attachment to connector 290, the elongated member 302 extends into lumen 296 to advance air through the air lumen into balloon 204 (or the pressure balloon in the embodiments with a single pressure balloon) to expand the balloon 204. That is, connection of the transducer hub 300 to the catheter 280 (port 282) automatically advances air through the connector lumen 296, the port lumen 283 and the first lumen 96 to expand the balloon 204. (Such connection also automatically connects the temperature sensor to the hub 300). In some embodiments, 0.2 cc of air can be displaced/advanced by the member 102, although other volumes are also contemplated. Thus, as can be appreciated, mounting of the hub 300 to the catheter 280 automatically pressurizes the air lumen/chamber and expands the balloon. Note the balloon can be partially or fully inflated (expanded), dependent on the amount of air advanced into the balloon. Further note that the lumen is not vented to atmosphere when the transducer hub 300 is attached and air is advanced through the air lumen. The port 282 includes a closable seal, e.g. valves 298 and 299, through which the elongated member 302 is inserted but maintains the seal when the elongated member 302 remains in the lumen 296. Note that catheter 290 is identical in all other respects to catheter 200 so that the description of catheter 200 and its components and function are fully applicable to catheter 280, the only difference being the connector 290 of catheter 292 to receive transducer hub 300. The hub 300 also differs from hub 240.

Figure 29A:
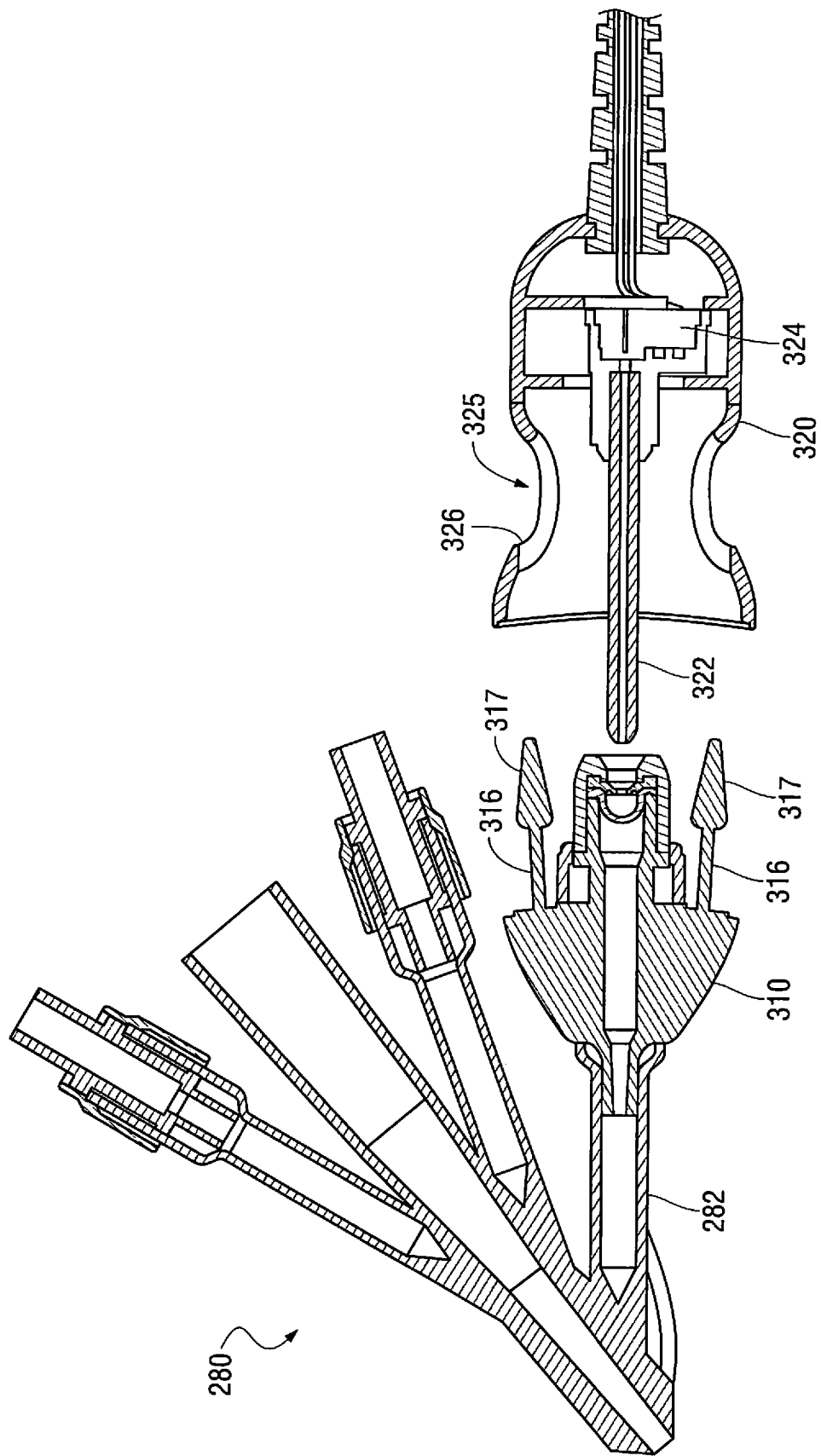
FIG. 29A is a cutaway side view of the hub and connector of an alternate embodiment showing the pressure transducer prior to connection to the catheter of FIG. 18A, a portion of the hub wall and connector removed to show internal components
Figure 29B:
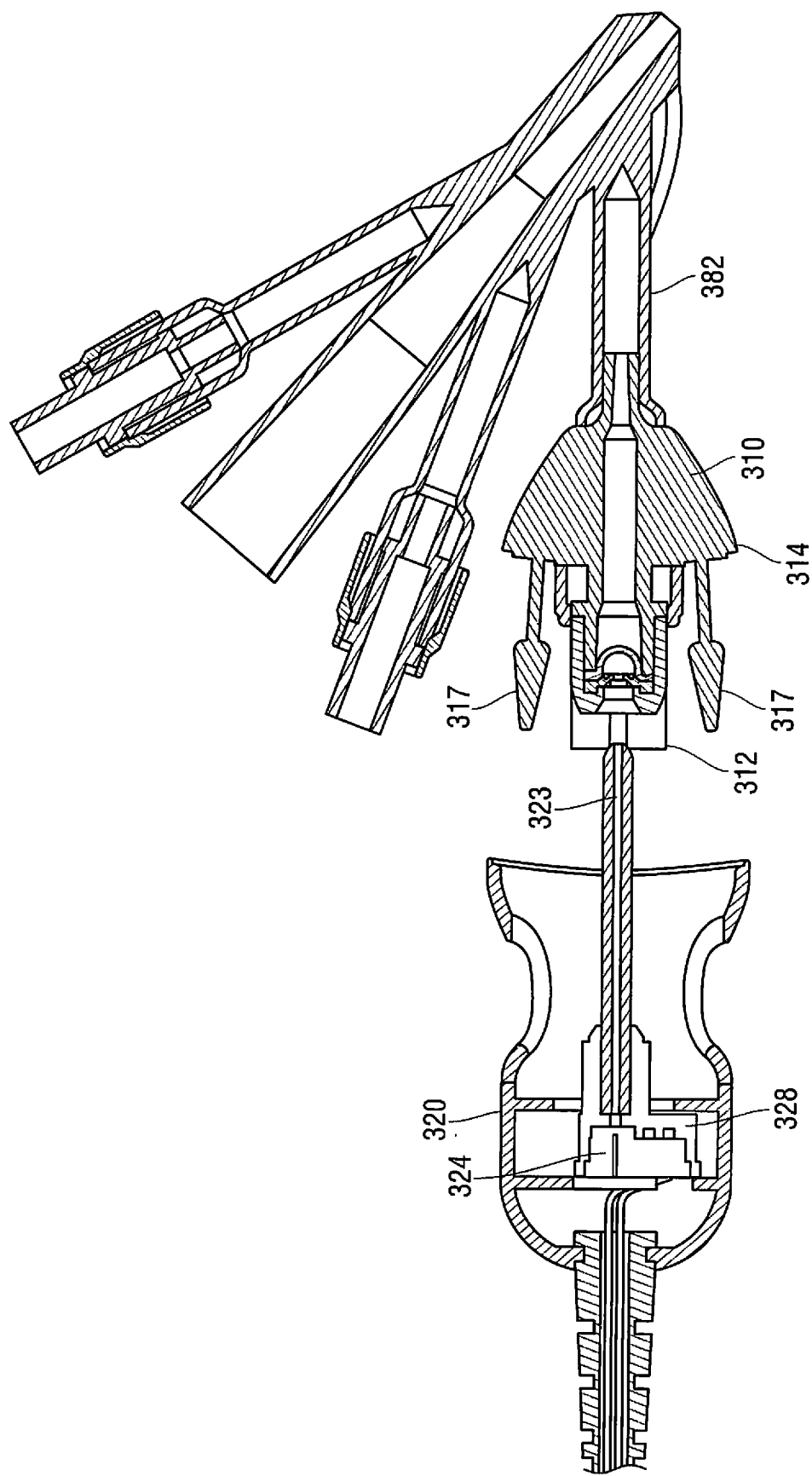
FIG. 29B is a cutaway view of the hub and connector of FIG. 29A from the other side.
Figure 29C:
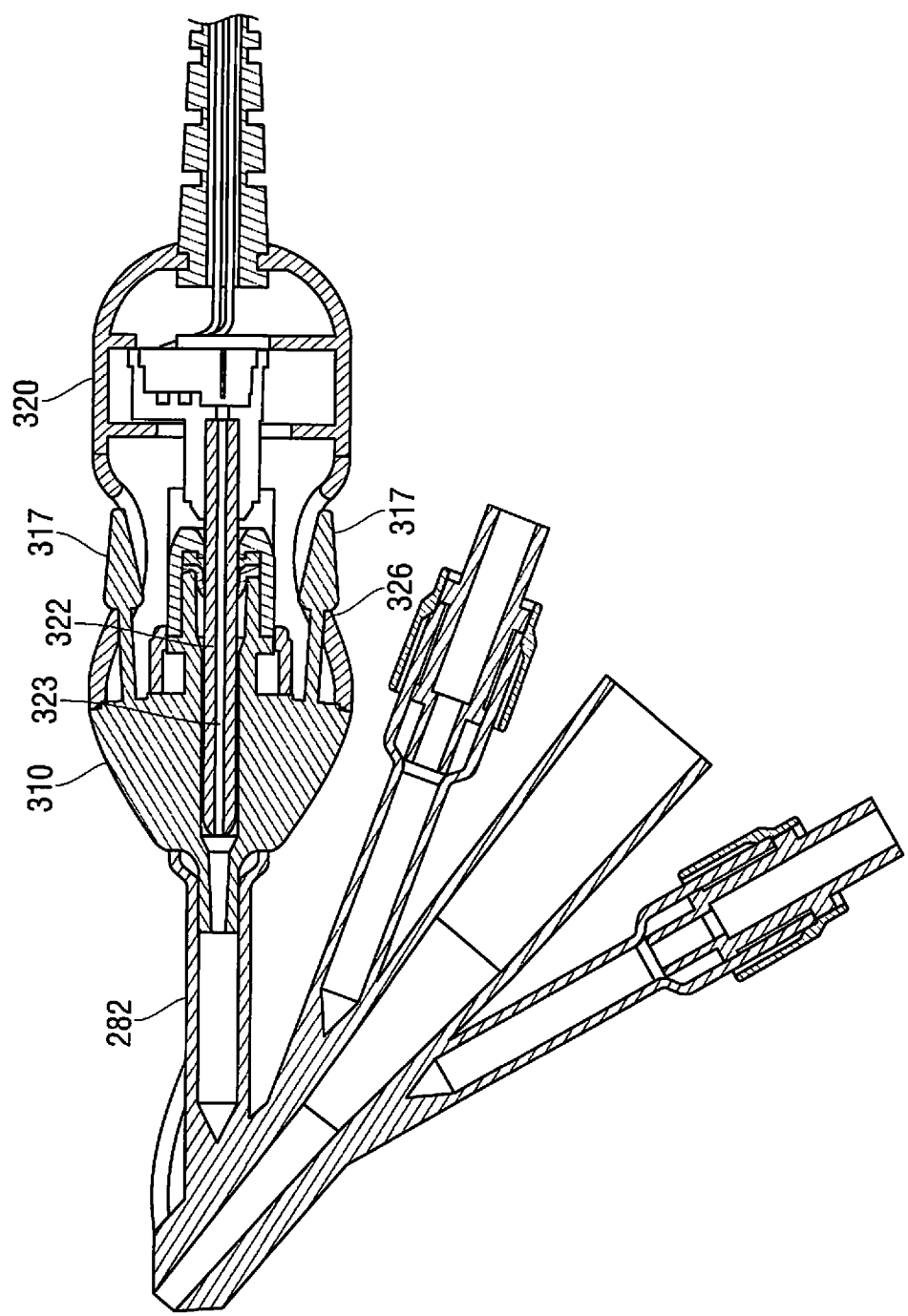
FIG. 29C is a cutaway view similar to FIG. 29B showing the hub attached to the catheter.

In the alternative embodiment of FIGS. 29A-29C, the latch arms are reversed so that they are located on the connector rather than on the transducer hub as in FIG. 28A. More specifically, transducer hub (housing), designated by reference numeral 320, has an elongated member 322 with a channel 323 and is identical to elongated member 302 of FIG. 28A for advancing air through the lumen and into the pressure balloon. Pressure transducer 324 is contained within the housing 320. Recesses 325 are dimensioned to receive the latch arms 317 of the connector or housing 310 which is connected to the side port 282 of catheter 280. (Catheter 280 is the same as catheter 280 of FIG. 28A except for connector 310). Extending proximally form housing 310 are two latch arms 316 with enlarged region 317 which engage the shoulders 326 formed by recesses 325 in hub 320 in a similar manner as latch arms 306 of FIG. 28A engage in recesses 291 and shoulder 291a, Connectors 328 in hub 320 engage thermistor pins 312 of connector 310 for connection of the temperature sensor. Connection of the hub 320, like hub 300, automatically advances air to inflate the pressure balloon and automatically connects the temperature sensor.

To disconnect the hub 320, ends 317 of latch arms 316 are pressed radially inwardly to disengage from shoulder 326 so hub 320 can be pulled proximally out of connector 310.

Note the lumen which is used to inflate the pressure balloon and create the air column has an opening at a distal region to communicate with the interior of the pressure balloon. If an outer balloon is provided, an additional lumen would be provided in the catheter to communicate with the outer balloon to fill the outer balloon and an additional angled port (extension) at the proximal end of the catheter would receive an inflation device to inflate, either fully or partially, the outer balloon.

Note in each of the embodiments disclosed herein, air is described as the preferred gas for creating the column and expanding the balloon, however, other gasses are also contemplated for each of the embodiments.

The pressure balloon can be symmetrically shaped as shown in some of the embodiments or alternatively shaped such that a distal region has an outer transverse cross-sectional dimension, e.g., diameter, greater than an outer transverse cross-sectional dimension, e.g., diameter, of the proximal region. A smooth transition (taper) can be provided between the distal region and proximal region, although other configurations are also contemplated. The inner (and outer) balloon can by way of example be made of urethane, although other materials are also contemplated.

The wire connector of the foregoing embodiments can plug into the openings of a connector positioned on or in the transducer hub. The wire connector can be internal of the hub with an opening in the wall of the hub to enable access for the wire connector. Also note that alternatively the wire can include a female connector and the hub can have a male connector. Other types of connectors/connections are also contemplated.

In alternate embodiments, any of the catheters disclosed here can include a pulse oximetry sensor to measure oxygen saturation in the urethral or bladder tissue. The sensor can be located either proximal or distal to the pressure balloon and/or stabilizing balloon. It could also alternatively be mounted within one of the balloons. A separate channel (lumen) could be provided for such sensor and wires.

In alternate embodiments, any of the catheters disclosed herein can include an additional channel (lumen) for continuously recording maternal PO2 and/or maternal respiration. Additionally, in alternate embodiments, any of the catheters disclosed herein can include a channel (lumen) for a sensor measuring fetal heart rate. Note each of the various sensors for measuring different parameters and their associated wires (unless wireless) can be provided in separate channels, or alternatively, one or more sensors and their associated wires can be provided in a single channel to reduce the overall size/diameter of the catheter. Thus, for example, a catheter with five or six lumens could be provided as follows: 1) lumen for expansion of outer balloon; 2) lumen for expansion of inner balloon and for pressure reading; 3) lumen for drainage of the bladder to a drainage bag; 4) lumen for expansion of the retention balloon; 5) lumen for the acoustic sensor to assess fetal heart rate; and 6) lumen for the pulse oximeter to measure maternal oxygen levels.

It is also contemplated that a backup system be provided to determine pressure. The backup system can provide a double check of pressure readings to enhance accuracy. Such backup system can be used with any of the embodiments disclosed herein to provide a second pressure reading system. One example of such backup system is disclosed in FIGS. 14A and 14B. In this embodiment, catheter 160 has the pressure transducer/pressure sensor 162 like sensor 30 of FIG. 1 within the air (or other gas) lumen 164 communicating with pressure balloon 167, forming a "first system", plus a pressure transducer/pressure sensor 169 at a proximal end of the catheter as in FIG. 12 or external of the catheter forming a "second system". Thus, the pressure sensor 162 is at a distal end of the air charged lumen 164 and pressure sensor 169 is at proximal end of the air charged lumen 164. Both sensors 162 and 169 are electrically connected to a monitor which provides a graphic display of pressure readings. The catheter 160 also includes a temperature sensor either as part of the sensor 162 or a separate component that can be positioned for example in the lumen 164 distal of sensor 162 as in the embodiment of FIG. 8. A stabilizing balloon 168 and an inflation lumen to inflate balloon 168 can also be provided. Lumen 163, having a side opening 170 at its distal end, is configured to drain the bladder similar to lumen 20 and side opening 22 of the embodiment of FIG. 1.

In use, catheter 160 is inserted into the bladder and stabilizing balloon 168 is inflated to secure the catheter 160 in place. The system is charged by inflation of the balloon 167, i.e., preferably partially inflated for the reasons discussed above, by insertion of air through side port 172 which is in fluid communication with the air lumen in a closed system formed by the internal space of the balloon 167 and the internal lumen 164 communicating with the internal space of balloon 167. With the balloon 167 inflated, pressure monitoring can commence as external pressure applied to an outer surface of the balloon 167 compresses the air (or other gas) within the chamber. The sensor 162 at the distal end of lumen 64 provides continuous pressure readings, converted to an electrical signal by the transducer within the distal end of the lumen, and then electrically communicates through its transmission wires extending through the air lumen to an external monitor either directly or via a converter. Additionally, pressure within the air charged column is measured at a proximal region by sensor 169 within side port 172 of catheter 160. The sensor 162 at the distal end of lumen 164 provides continuous pressure readings, and such pressure readings can be confirmed by the proximal sensor. Such pressure readings can be performed continuously (along with continuous temperature monitoring) or alternatively can also be adapted if desired for periodic monitoring so the pressure and/or temperature readings can be taken at intervals or on demand by the clinician. Thus, air pressure readings at a proximal end plus microtip pressure readings at the distal end are provided. The sensors 162 and 169 can electrically communicate with an external monitor to display both pressure readings from sensors 162, 169, or alternatively, if the pressure readings are different, they can be averaged to display a single measurement. Clearly, other displays of information can be provided to display the information from the two sensors 162, 169.

The sensors disclosed herein can be microtip sensors within the air lumen or balloon. In alternative embodiments, fiber optic sensors within the air lumen or within or around the balloon can by utilized to transmit circumferential/area pressure exerted on the bladder. The pressure transducers can be housed within the catheter or alternatively external to the catheter. Additionally, core temperature sensors can be part of the pressure sensor or a separate axially spaced component.

The multi-lumen catheters disclosed herein provide an air (or other gas) charged balloon giving precise readings of uterine contraction pressure and core temperature and the systems are charged via insertion of air through a side port via a syringe in a gross fashion or through displacement of air in the lumen. The multi-lumen catheters are easily inserted into the bladder in the same manner as standard bladder drainage catheters and enable continuous drainage of urine while continuously recording uterine contraction pressure without interrupting urine flow and without requiring retrograde filling of the bladder with water. Thus, these catheters provide a closed system. The catheters also have a balloon providing a large reservoir (large capacity) and large circumferential area/interface for obtaining more information from the bladder over multiple reference points (rather than a single point sensor) that provides an average pressure to provide a gross measurement and a more accurate assessment of the surrounding environment as pressure measurement is not limited to one side of the bladder but can determine measurements on the opposing side as well.

As noted above, the catheters, i.e. the transducer, can be connected to a bedside monitor through either a wire or blue-tooth wireless connection. Such wireless connection would provide the patient the option to ambulate while in labor.

The system can also include an indicator or alarm system to alert the staff at the site as well as remote staff through wired or wireless connections to external apparatus, e.g., hand held phones or remote monitors.

As noted above, an alarm or indicator can be provided in some embodiments to alert the staff. The indicator can be a visual indicator such as a light, LED, color change, etc. Alternatively, or additionally, the indicator can be an audible indicator which emits some type of sound or alarm to alert the staff. The indicator can be at the proximal region of the catheter or at other portions of the catheter, e.g., at a distal end portion, where known imaging techniques would enable the user to discern when the indicator is turned on. It is also contemplated that in addition to providing an alert to the user, the pressure or other monitoring system can be tied into a system to directly control parameters so that if the pressure or other parameter is outside a desired range, appropriate steps can be taken. In such systems, one or more indicators can be provided on the proximal portion of the catheter, e.g., at a proximal end outside the patient's body, or separate from the catheter. The sensor(s) is in communication with the indicator(s), either via connecting wires extending through a lumen of the catheter or a wireless connection. The sensor(s) can be part of a system that includes a comparator so that a comparison of the measured pressure or other parameter, e.g., maternal core body temperature, maternal PO2 levels, fetal heart rate, etc. to a predetermined value is performed and a signal is sent to the indicator to activate (actuate) the indicator if the measured pressure value or other value is exceeded, thereby alerting the clinician or staff that pressure or other parameters are outside desired ranges and a signal is also sent to a device or system to automatically actuate the device or system to make the necessary adjustments. If the measured value is below the threshold, the indicator is not activated.

As noted above, the catheters of the present invention can be inserted in the same manner as the regular urinary bladder drainage catheter. Thus the catheters do not require any special nursing or physician skills for insertion and use. Thus, the catheters can be easily inserted by any provider on labor and delivery ward with the skills to insert a simple bladder drainage catheter.

As noted above, the catheters may be used to precisely detect contractions in mothers with symptoms of preterm labor. They can be used to detect adequacy of labor in mothers that are not normally progressing in labor. They can be used to help detect pressure in mothers presenting with signs of pre-eclampsia (PE). It has been found that detection of pressure in patients with PE can help diagnose and prevent maternal health complications or death. In some embodiments as noted above, specialized sensors in the catheter will help detect maternal oxygenation which is important to monitor in all laboring patients. The catheters as noted above can in some embodiments also have the capability to detect maternal respiration and/or fetal heart rate. The catheters in some embodiments can have an acoustic sensor to pick up fetal heart tones.

It is also contemplated that a micro-air charged sensor could be provided in the retention (stabilizing) balloon to help detect fetal heart rate.

It is also contemplated that microtip sensors and/or fiber optic sensors can be utilized to measure pressure, and these sensors can be utilized instead of the air pressure readings utilizing the aforedescribed balloon(s) for measuring pressure.

The catheters disclosed herein are designed for insertion into the bladder. However, it is also contemplated that they can be adapted for insertion into other body regions.

Although the apparatus and methods of the subject invention have been described with respect to preferred embodiments, those skilled in the art will readily appreciate that changes and modifications may be made thereto without departing from the spirit and scope of the present invention as defined by the appended claims.

What is claimed is:

1. A multi-lumen catheter for monitoring uterine contraction pressure, the catheter comprising:
    an expandable outer balloon at a distal portion of the catheter, the outer balloon having a first outer wall;
    an expandable inner balloon positioned within the outer balloon, the inner balloon having a second outer wall;
    a first lumen communicating with the inner balloon, the inner balloon and first lumen forming a gas filled chamber to monitor pressure within a bladder to thereby monitor uterine contraction of the patient, wherein the outer balloon has a circumferential area greater than a circumferential area of the inner balloon, wherein in response to pressure within the bladder exerted on the first outer wall of the expanded outer balloon, the outer balloon deforms and exerts a pressure on the second outer wall of the expanded inner balloon to deform the inner balloon and compress the gas within the inner balloon and the first lumen to provide a finer measurement; and
    a second lumen communicating with the bladder to remove fluid from the bladder;
    wherein pressure is measured based on gas compression caused by deformation of the expanded inner balloon deformed by the expanded outer balloon, the bladder pressure providing an indication of uterine contraction pressure.

2. The catheter of claim 1, wherein the outer balloon has a circumference engageable with a wall of the bladder at multiple contact regions to provide multiple reference points for calculation of an average pressure of the bladder wall.

3. The catheter of claim 1, wherein a pressure transducer contained within a hub is connected to a first port of the catheter and such connection to the first port automatically advances air into the inner balloon to expand the inner balloon, the pressure transducer communicating with the air filled chamber.

4. The catheter of claim 3, wherein the first lumen is not vented to atmosphere when the pressure transducer is connected to the catheter and advances air to expand the inner balloon.

5. The catheter of claim 3, further comprising a temperature sensor and a wire extending proximally from the temperature sensor, and the hub has a first opening to receive a connector of the wire to automatically connect the temperature sensor to a cable extendable from the hub and connectable to an external temperature monitor.

6. The catheter of claim 3, wherein after initial advancement of air into the first lumen by the elongated member upon connection of the pressure transducer, additional air does not need to be inserted during the duration of insertion of the catheter in a body of a patient.

7. The catheter of claim 1, wherein the second lumen has a side opening distal of the inner and outer balloons.

8. The catheter of claim 1, wherein the second lumen has a side opening proximal of the inner and outer balloons.

9. The catheter of claim 1, wherein the catheter further comprises a third lumen communicating with the outer balloon to expand the outer balloon.

10. The catheter of claim 1, wherein the catheter has one or more of a temperature sensor positioned to measure core body temperature, a fetal heart rate sensor to detect fetal heart rate, and a PO2 sensor positioned to measure PO2 levels.

11. The catheter of claim 1, further comprising a stabilizing balloon proximal of the outer balloon for stabilizing the catheter, and the catheter includes an additional lumen communicating with the stabilizing balloon to expand the stabilizing balloon.

12. The catheter of claim 1, wherein the outer balloon has a distal region having a larger transverse cross-section than a proximal region.

13. A system for monitoring uterine contraction pressure including a catheter and a hub connectable to the catheter, the system comprising:
    a distal balloon at a distal portion of the catheter;
    a first lumen communicating with the distal balloon, the distal balloon and first lumen forming an air filled chamber to monitor pressure within a bladder to thereby monitor uterine contraction pressure of a patient, wherein in response to pressure within the bladder the distal balloon deforms to compress the air within the distal balloon, the first lumen having a first proximal port communicating with the first lumen;
    a second lumen communicating with the bladder to remove fluid from the bladder; and
    the hub is connectable to a first port of the catheter, the hub including a pressure transducer for measuring pressure based on air compression with the first lumen, wherein connection of the hub to the first port automatically advances air through the first lumen to expand the distal balloon, the first lumen not vented to atmosphere when the hub is connected to the first port so the first lumen remains sealed to outside air during expansion of the distal balloon.

14. The system of claim 13, further comprising temperature sensor positioned in the catheter and having a wire extending through the catheter, wherein connection of the hub to the first port automatically connects the wire to an electrical connector in the hub for connection to a temperature monitor.

15. The system of claim 14, further comprising a stabilizing balloon proximal of the distal balloon for stabilizing the catheter.

16. The system of claim 15, wherein the catheter includes a second lumen has a side opening between the distal balloon and the stabilizing balloon.

17. The system of claim 14, wherein the catheter includes one or both of a fetal heart rate sensor proximal to the outer balloon to detect fetal heart rate and a PO2 sensor proximal to the outer balloon to detect PO2 levels.

18. A method for measuring uterine contraction pressure comprising the steps of:
providing a catheter having first and second lumens, an expandable first balloon, an expandable second balloon positioned over the first balloon, and a temperature sensor;
inserting the catheter into a bladder of a patient;
connecting a hub containing a pressure transducer to the catheter to automatically advance air through the first lumen of the catheter to expand the first balloon from a deflated condition to a more expanded condition;
obtaining a first pressure reading of the bladder based on deformation of the first balloon caused by deformation of the second balloon in response to bladder pressure exerted on the second balloon, the bladder pressure measurement providing an indication of uterine contraction pressure;
transmitting the first pressure reading to an external monitor connected to the hub to assess uterine contraction pressure;
obtaining a second pressure reading of the bladder based on deformation of the first balloon caused by deformation of the second balloon in response to bladder pressure exerted on the second balloon; and
transmitting the second pressure reading to the external monitor connected to the hub to assess uterine contraction pressure.

19. The method of claim 18, wherein the step of connecting the hub automatically connects the temperature sensor to a connector within the hub.

20. The method of claim 18, wherein the catheter includes a first sensor and a second sensor, and further comprising the step of measuring one or both of fetal heart rate via the first sensor and maternal PO2 levels via the second sensor.

* * * * *